(12) United States Patent
Mir et al.

(10) Patent No.: US 10,244,981 B2
(45) Date of Patent: Apr. 2, 2019

(54) SKIN TEST IMAGE ANALYSIS APPARATUSES AND METHODS THEREOF

(75) Inventors: Jose Mir, Rochester, NY (US); John Spoonhower, Webster, NY (US); John A. Agostinelli, Rochester, NY (US); John Squilla, Penfield, NY (US)

(73) Assignee: SENSIVIDA MEDICAL TECHNOLOGIES, INC., West Henrietta, NY (US)

( * ) Notice: Subject to any disclaimer, the term of this patent is extended or adjusted under 35 U.S.C. 154(b) by 0 days.

(21) Appl. No.: 13/272,966

(22) Filed: Oct. 13, 2011

(65) Prior Publication Data
US 2012/0253224 A1  Oct. 4, 2012

Related U.S. Application Data

(63) Continuation of application No. 13/076,182, filed on Mar. 30, 2011, now abandoned.

(51) Int. Cl.
*A61B 5/00* (2006.01)
*A61K 45/06* (2006.01)

(52) U.S. Cl.
CPC ............ *A61B 5/441* (2013.01); *A61B 5/0077* (2013.01); *A61B 5/0053* (2013.01); *A61B 5/442* (2013.01)

(58) Field of Classification Search
USPC ........................................ 600/556, 300, 426
See application file for complete search history.

(56) References Cited

U.S. PATENT DOCUMENTS

| 4,161,176 A | * | 7/1979 | Harris et al. ..................... 602/58 |
| 4,228,796 A | * | 10/1980 | Gardiner ....................... 604/116 |
| 4,366,500 A | * | 12/1982 | Kurtz et al. ................... 358/505 |

(Continued)

FOREIGN PATENT DOCUMENTS

| DE | 19610293 C1 | 7/1997 |
| EP | 0299778 A3 | 1/1989 |

(Continued)

OTHER PUBLICATIONS

Ahn, Chong H., "Micromachined Planar Inductors on Silicon Wafers for MEMS Applications"; pp. 866-876; IEEE Transactions on Industrial Electronics, vol. 45, No. 6, Dec. 1998.

(Continued)

Primary Examiner — May A Abouelela
(74) Attorney, Agent, or Firm — LeClairRyan PLLC

(57) ABSTRACT

An apparatus and method for making an apparatus for skin testing includes a housing with an opening which defines a field of view of a skin testing region, an image sensing apparatus, an illumination apparatus, a binding apparatus, and an image processing controller. The image sensing apparatus is positioned with respect to the housing to capture images in the field of view provided by the opening. The illumination apparatus is positioned within the housing to direct light towards a portion of the field of view provided by the opening. The binding apparatus detachably secures the housing over the skin testing region and maintains a fixed distance between the image sensing apparatus and the skin testing region. The controller is configured to analyze test samples sites in each of the captured images from the image sensing apparatus and provide a skin test result for each of the test sample sites.

32 Claims, 31 Drawing Sheets

(56) References Cited

U.S. PATENT DOCUMENTS

| | | | |
|---|---|---|---|
| 4,862,894 A * | 9/1989 | Fujii | 600/479 |
| 4,871,351 A | 10/1989 | Feingold | |
| 5,054,896 A | 10/1991 | Margolis | |
| 5,097,810 A * | 3/1992 | Fishman et al. | 600/556 |
| 5,099,857 A | 3/1992 | Baldo et al. | |
| 5,380,272 A * | 1/1995 | Gross | 604/20 |
| 5,457,041 A | 10/1995 | Ginaven et al. | |
| 5,680,858 A | 10/1997 | Hansen et al. | |
| 5,741,211 A | 4/1998 | Renirie et al. | |
| 5,928,268 A | 7/1999 | Butwell et al. | |
| 5,953,411 A | 9/1999 | Farrell | |
| 5,971,963 A | 10/1999 | Choi | |
| 6,024,925 A * | 2/2000 | Little et al. | 422/507 |
| 6,083,196 A * | 7/2000 | Trautman et al. | 604/46 |
| 6,142,939 A * | 11/2000 | Eppstein et al. | 600/309 |
| 6,292,576 B1 | 9/2001 | Brownlee | 382/124 |
| 6,319,467 B1 * | 11/2001 | McLernon, III | 600/556 |
| 6,355,054 B1 | 3/2002 | Neuberger | |
| 6,540,675 B2 | 4/2003 | Aceti et al. | |
| 6,587,711 B1 * | 7/2003 | Alfano et al. | 600/476 |
| 6,624,847 B1 * | 9/2003 | Abdellatif | 348/223.1 |
| 6,692,456 B1 * | 2/2004 | Eppstein et al. | 604/22 |
| 6,887,202 B2 | 5/2005 | Currie et al. | |
| 6,923,764 B2 * | 8/2005 | Aceti et al. | 600/309 |
| 6,934,438 B2 * | 8/2005 | Hoke | 385/16 |
| 7,004,928 B2 * | 2/2006 | Aceti et al. | 604/191 |
| 7,132,054 B1 | 11/2006 | Kravitz et al. | |
| 7,392,080 B2 * | 6/2008 | Eppstein et al. | 604/20 |
| 7,512,432 B2 * | 3/2009 | Zocchi | 600/347 |
| 7,585,578 B2 | 9/2009 | Yonekura et al. | |
| 7,713,234 B2 * | 5/2010 | Karanzas | 604/116 |
| 7,798,976 B2 * | 9/2010 | Niklasson | 600/556 |
| 8,075,525 B2 * | 12/2011 | Yang | 604/116 |
| 8,116,860 B2 * | 2/2012 | Messier et al. | 604/20 |
| 8,363,259 B2 * | 1/2013 | Gilboa | 358/1.18 |
| 8,404,255 B2 * | 3/2013 | Gibson et al. | 424/400 |
| 2002/0002326 A1 * | 1/2002 | Causey et al. | 600/300 |
| 2002/0013849 A1 | 1/2002 | Schweitzer et al. | |
| 2002/0087056 A1 * | 7/2002 | Aceti et al. | 600/309 |
| 2003/0083680 A1 | 5/2003 | Jousson | |
| 2003/0083686 A1 | 5/2003 | Freeman et al. | |
| 2003/0153900 A1 | 8/2003 | Aceti et al. | |
| 2003/0208113 A1 | 11/2003 | Mault et al. | |
| 2003/0208167 A1 | 11/2003 | Prausnitz et al. | |
| 2003/0218756 A1 | 11/2003 | Chen et al. | |
| 2004/0096959 A1 | 5/2004 | Stiene et al. | |
| 2004/0138541 A1 * | 7/2004 | Ward et al. | 600/345 |
| 2004/0176701 A1 | 9/2004 | Fujii | |
| 2005/0070819 A1 | 3/2005 | Poux et al. | |
| 2005/0137531 A1 | 6/2005 | Prausnitz et al. | |
| 2005/0137536 A1 | 6/2005 | Gonnelli | |
| 2005/0171480 A1 | 8/2005 | Mukerjee et al. | |
| 2005/0182307 A1 | 8/2005 | Currie et al. | |
| 2005/0209565 A1 * | 9/2005 | Yuzhakov et al. | 604/173 |
| 2005/0228313 A1 | 10/2005 | Kaler et al. | |
| 2005/0228340 A1 * | 10/2005 | Cleary et al. | 604/46 |
| 2005/0256499 A1 | 11/2005 | Pettis et al. | |
| 2006/0002636 A1 | 1/2006 | Torre-Bueno et al. | |
| 2006/0047242 A1 * | 3/2006 | Laurent et al. | 604/46 |
| 2006/0049209 A1 | 3/2006 | Baker | |
| 2006/0094985 A1 * | 5/2006 | Aceti et al. | 600/575 |
| 2006/0167375 A1 * | 7/2006 | Terrassse et al. | 600/556 |
| 2006/0219576 A1 * | 10/2006 | Jina | 205/792 |
| 2007/0092496 A1 | 4/2007 | Zheng et al. | |
| 2007/0100255 A1 * | 5/2007 | Boecker et al. | 600/583 |
| 2007/0110672 A1 | 5/2007 | Bellott et al. | |
| 2007/0276211 A1 * | 11/2007 | Mir et al. | 600/345 |
| 2007/0276284 A1 * | 11/2007 | Utsugi | 600/556 |
| 2008/0214952 A1 * | 9/2008 | Mir et al. | 600/556 |
| 2008/0269635 A1 * | 10/2008 | Mir et al. | 600/556 |
| 2009/0118638 A1 * | 5/2009 | Schindlbeck et al. | 600/556 |
| 2009/0290174 A1 * | 11/2009 | Gilboa | 358/1.9 |
| 2009/0295910 A1 * | 12/2009 | Mir et al. | 348/61 |
| 2010/0022910 A1 * | 1/2010 | Lane et al. | 600/556 |
| 2010/0030100 A1 * | 2/2010 | Tokumoto et al. | 600/556 |
| 2010/0121307 A1 * | 5/2010 | Lockard | A61M 37/0015 604/506 |
| 2010/0284583 A1 * | 11/2010 | Ljung | 382/128 |
| 2011/0264003 A1 * | 10/2011 | Hamann | 600/556 |
| 2012/0027810 A1 * | 2/2012 | Chen | A61M 37/0015 424/400 |

FOREIGN PATENT DOCUMENTS

| | | |
|---|---|---|
| EP | 1086718 B1 | 3/2001 |
| GB | 2309644 A | 8/1997 |
| WO | WO0180728 A1 | 11/2001 |
| WO | WO03092487 A1 | 11/2003 |

OTHER PUBLICATIONS

Cula, et al., "Bidirectional Imaging and Modeling of Skin Texture", Proceedings of Texture 2003, Oct. 17, 2003, Nice, France, 6 pgs.

Damean, Nicolae, "Composite ferromagnetic photoresist for the fabrication of microelectromechanical systems", pp. 29-34; Institute of Physics Publishing; 2005 IOP Publishing Ltd.

DFW-V500, Technical Manual (Ver. 1.0).

Grimes, C.A., "Magnetoelastic sensors for remote query environmental monitoring", Smart Mater. Strut. 8 (1999), pp. 639-646; UK.

Hunter, Ian, "Minimally Invasive Glucose Sensor and Insulin Delivery System", pp. 1-17; Phase 2 Final Report: Sep. 30, 2000; MIT Home Automation and Healthcare Consortium.

Litwiller, Dave, "CCD vs. CMOS: Facts and Fiction", Jan. 2001 Photonics Spectra.

Ong, K.G., "Magnetism-Based Remote Query Glucose Sensors", SENSORS 2001, 1, 138-147; http://www.mdpi.net/sensors.

Prinz, et al., "Automatic Measurement of Skin Wheals Provoked by Skin Prick Tests", Connecting Medical Informatics and Bio-Informatics, IOS Press, 2005; EFMI, pp. 441-446.

Proximity Series. InfiniMini.

Schuster et al., "Macro-Video Documentation Patch Tests", Contact Dermatitis 2005: 52:177-183.

Stout, Michael C., Office Action from the United States Patent and Trademark Office for U.S. Appl. No. 11/995,366 (dated Apr. 29, 2010).

Alksne John F., "The Passage of Colloidal Particles Across the Dermal Capillary Wall Under the Influence of Histamine," Department of Anatomy, University of Washington, Seattle 5, Washington, Aug. 1958, 44(1) pp. 51-66.

Baluk et al., "Endothelial Gaps and Adherent Leukocytes in Allergen-Induced Early and Late-Phase Plasma Leakage in Rat Airways," American Journal of Pathology, Jun. 1998, vol. 152, No. 6, pp. 1463-1476.

"Debiotech received a Swiss Technology Award 2006 and the Vontobel Prize for its novel Insulin Pump and microneedle patch," Last accessed, Jun. 1, 2006, Debiotech.com/news, pp. 1-3. (http://www.debiotech.com/news).

Dreborg, S., "Histamine reactivity of the skin," Editorial, Dec. 5, 2000, 56: pp. 359-364.

Ghidalia et al., "Overall Study of the in Vitro Plasma Clotting System in an Invertebrate, Liocarcinus puber (Crustacea Decapoda): Considerations on the Structure of the Crustacea Plasma Fibrinogen in Relation to Evolution," Journal of Invertebrate Pathology,1989, vol. 53: pp. 197-205, Academic Press, Inc.

Kravitz, Stanley, H., et al., "A Quick, Reliable, and Versatile Method for Creating Microneedles for Bio-Harvesting," 2004 Joint International Meeting on Microfab., Oct. 4, 2004, Sandia National Laboratories, Albuquerque, NM.

Kuo, Shyh-Chyi, et al., "A Novel Polymer Microneedle Arrays and PDMS Micromolding Technique," Tamkang Journal of Science & Engineering, 2004, vol. 7 No. 2, pp. 95-98.

Majno et al., "Endothelial Contraction Induced by Histamine-Type Mediators—An Electron Microscopic Study," Article of the Journal of Cell Biology, Sep. 1, 1969, vol. 42, pp. 647-672.

Michel et al., "Microvascular Permeability," Physiological Reviews, Jul. 1999, vol. 79, No. 3, pp. 703-761, The American Physiological Society, USA.

(56) References Cited

OTHER PUBLICATIONS

Michel et al., "Differing effects of histamine and serotonin on microvascular permeability in anaesthetized rats," Journal of Physiology, 1997, vol. 501.3, pp. 657-662.

Milne et al., "Role of Serotonin in Blood Coagulation," U.S. Naval Radiological Defense Laboratory, San Francisco, California, Jan. 7, 1957, pp. 470-474.

Neal et al., "Transcellular gaps in microvascular walls of frog and rat when permeability is increased by perfusion with the ionophore A23187," Journal of Physiology,1995, vol. 488, No. 2, pp. 427-437.

Paquit et al., "Near-infrared imaging and structured light ranging for automatic catheter insertion," 2006, pp. 1-9, Oak Ridge National Laboratory, Oak Ridge, Tennessee, USA.

Ramaswamy et al., "Microfluidic device and system for point-of-care blood coagulation measurement based on electrical impedance sensing," Sensors and Actuators B: Chemical, Nov. 2011, 7 pgs, Elsevier B.V.

Renkin, E.M., "Multiple pathways of capillary permeability," Circulation Research, Publication,1977, vol. 41, pp. 735-743, American Heart Association, USA.

Sandia National Laboratories "Electroneedle® Biomedical Sensor Array", R&D 100 Award Entry 2007, (2007) 1053, pp. 1-25.

Sarin, Hemant, "Physiologic upper limits of pore size of different blood capillary types and another perspective on the dual pore theory of microvascular permeability," Journal of Angiogenesis Research, 2010, vol. 2:14.

Tonnesen, P., "Intracutaneous and Skin Prick Testing with Serotonin and Histamine," Allergy, 1986, vol. 41, pp. 196-202.

Trautmann et al., "Transducers '05. The 13th International Conference on Solid-State Sensors, Actuators and Microsystems" Digest of Technical Papers, 2005, pp. 1420-1423, Seoul, Korea.

Wang, Ping M., et al., "Minimally Invasive Extraction of Dermal Interstitial Fluid for Glucose Monitoring Using Microneedles," Diabetes Tech. & Therapeutics, 2005, vol. 7, No. 1. pp. 131-142.

Zhao et al., "Quantitative correlations among fibrinogen concentration, sedimentation rate, and electrical impedance of blood," Medical & Biological Engineering & Computing, May 1997, vol. 35, pp. 181-185.

Zhou et al., "Impedance Analysis of Blood Coagulation by Prothrombin Time Assay in a Miniature Device," ICMM2005-75155, 3rd International Conference on Microchannels and Minichannels (ICMM2005), ASME, Jun. 13-15, 2005, pp. 737-741, Toronto,Ontario, Canada.

Zimmerman, Stefan, et al., "A Microneedle-Based Glucose Monitor: Fabricated on a Wafer-Level Using In-Device Enzyme Immobilization," The 12th International Conference on Solid State Sensors, Actuators and Microsystems, Jun. 8, 2003, pp. 99-102, Boston, MA, USA.

Bahna S., "Allergy Skin Testing Techniques," Presentation for WAO International Scientific Conference, Dubai India Dec. 2010.

Dreborg, S., "Art and Science of Percutaneous Skin Testing," Course 165 American Academy if Allergy, Asthma & Immunology, Orlando Florida Mar. 2, 2012.

Nelson, H., "Effect of Distance Between Sites and Region of the Body on Results of Skin Prick Tests," Journal Allergy Clinical Immunology 97:596-601 (1996).

Nagao-Dias et al., "Implementation of a Penicillin Allergy Skin Test," Brazilian Journal of Pharmaceutical Sciences 45 (3):567-572.

* cited by examiner

170

172

176

180

176

150

152

156

154

158

SKIN TEST IMAGE ANALYSIS APPARATUSES AND METHODS THEREOF

This application is a continuation-in-part of prior application Ser. No. 13/076,182, filed Mar. 30, 2011, which is herein incorporated by reference.

FIELD

This invention generally relates to systems and methods for biomedical image analysis, and more specifically, to systems and methods for skin test image analysis.

BACKGROUND

Image processing used for skin assessment, such as for measurement of an allergic or skin reaction during standard Skin Prick Testing, is hampered by a number of variables that are often not well controlled and can even be inconsistent within a typical medical dermatology or allergy practice. Specific variables that can affect measurement accuracy include the following:

Lighting conditions: Ambient light can vary due to variables such as type of fluorescent or incandescent light source used, illumination angle, and collimation of light illuminating the subject's arm or back, to name a few.

Visual acuity and skill of nurse or other practitioner: Depending on the visual acuity and judgment of the practitioner administering the allergy test or performing other skin imaging, measurement variability can result even under well-controlled lighting conditions. Even among well-trained professionals, the resulting measurement is ultimately subjective due to differences in criteria and judgment for wheal/flare visibility.

Irregularity and asymmetry of reactions: Wheal features, geometries, and dimensions, including pseudopodia and other irregular skin reactions can vary from one patient to the next. Such irregularity complicates quantification of reaction extent.

Differences in patient skin tone and overall skin condition: Skin color, differences in overall melanin content, aging, and other factors complicate the task of achieving a consistent basis for measurement, including measurements of change in reaction over time.

As is well known to those who study the subject in detail, human skin is itself highly variable from one person to the next and exhibits significant differences even over different areas of the same person. The task of making accurate measurements of features on the skin surface is highly complex when compared with making comparable measurements of relatively homogeneous surfaces. The complexity of this task is particularly appreciated by practitioners who test skin response for determining allergic sensitivity. Current test methods that analyze test results using the human eye can be cumbersome, inaccurate, and time-consuming, as well as uncomfortable for the patient. The accuracy of current manual test methods is disappointing. There is a significant chance of error due to the complicated nature of the steps involved in executing the test sequence and analyzing results. Coupled with these problems is the overall difficulty of getting patients into an office for testing, particularly for elderly or pediatric patients, and for underserved patient populations.

Current skin prick testing for allergic reaction requires using extensive amounts of the skin surface area. For example, the conventional skin prick test for 24 different allergens requires use of both arms of a typical patient, with as much as 1 or more inches between each skin prick site. Improvements for more efficient testing have been proposed, such as the skin test device described in U.S. Pat. No. 5,099,857 entitled "Medical Testing Device with Calibrated Indicia" to Baldo et al. (Baldo '857) that packages a number of capsules and needles for allergen testing in a single patch. Baldo '857 states that a minimum distance between capsule/needle units should be about 20 mm, so that a 4×6 test patch array with 24 skin prick sites would require an area of the skin of at least about 80×120=9600 mm$^2$.

Conventional testing methods are disclosed in a reference paper relating to image processing on wheals: "Automatic Measurement of Skin Wheals Provoked by Skin Prick Tests", Stud. Health Technol. Infor. 2005, Vol 116, pp 441-446 by M. Prinz, K. Vigl, and S. Wohrl. In this case, wheals are identified, and their outlines marked on a separate sheet for transfer to a computer scan able medium. The process requires manual identification and outlining of the wheal dimensions. It is time-consuming and is prone to the same human measurement errors as the standard skin prick test. It is impractical to use this method for small wheal diameter measurement.

There is a need to have a means to interpret and analyze skin response data in a consistent and straightforward manner that provides improved accuracy over existing methods. What is desired is an easy and consistent methodology to automatically analyze the image data obtained by allergy testing.

SUMMARY

An apparatus for skin testing includes a housing with an opening which defines a field of view of a skin testing region, an image sensing apparatus, an illumination apparatus, a binding apparatus, and an image processing controller. The image sensing apparatus is positioned with respect to the housing to capture one or more images in the field of view provided by the opening in the housing. The illumination apparatus is positioned within the housing to direct light towards at least a portion of the field of view provided by the opening in the housing. The binding apparatus detachably secures the housing with the opening over the skin testing region and maintains a substantially fixed optical distance between the image sensing apparatus and the skin testing region. The image processing controller is configured to analyze two or more test samples sites which are spaced fifteen mm or less apart in the field of view in each of the one or more captured images from the image sensing apparatus and provide a skin test result for each of the two or more test sample sites.

A method for making an apparatus for skin testing includes providing a housing with an opening which defines a field of view of a skin testing region. An image sensing apparatus is positioned with respect to the housing to capture one or more images in the field of view provided by the opening in the housing. The illumination apparatus is positioned with respect to the housing to direct light towards at least a portion of the field of view provided by the opening in the housing. A binding apparatus is provided that detachably secures the housing with the opening over the skin testing region and maintains a substantially fixed optical distance between the image sensing apparatus and the skin testing region. An image processing controller is provided that is configured to analyze two or more test samples sites which are spaced fifteen mm or less apart in the field of view in each of the one or more captured images from the image sensing apparatus and provide a skin test result for each of the two or more test sample sites.

The present invention addresses the need for improved accuracy and ease of use of allergy testing and other skin measurement devices. By utilizing the present invention, an allergy test evaluation can produce significantly more precise and accurate results. This invention provides a number of advantages.

Some examples of the apparatus of the present invention strictly control skin test parameters since the illumination and imaging components are invariant test-to-test and are independent on the judgment of persons administering the test. For these reasons, digital measurements are substantially more reproducible and accurate than conventional visual/subjective methods for allergy and skin testing.

The digital imaging system and methods described herein help to reduce the impact of human subjectivity and visual acuity as variables, thereby resulting in improved measurement accuracy. This enables faster evaluation, reduced training requirements, and allows analysis from locations removed from the test site.

Among other advantages offered by the apparatus of the present invention are measurement methods that can help to reduce the impact of skin coloration on measurement accuracy. Reaction dimensions and color changes as well as contour changes can be measured quantitatively with improved accuracy and consistency over existing methods. The area of the skin that is needed for testing response to a number of allergens is a small fraction of the minimum required using conventional methods. In addition, kinetic data showing rates of change in reaction response can also be obtained with improved accuracy.

These advantages can be realized by a method for skin testing including: obtaining one or more baseline images of a skin test area; obtaining an assessment image of the skin test area; subtracting the baseline image from the assessment image to produce a difference image; reducing image noise in the difference image; applying a contrast stretch function to the difference image to produce a contrast stretched difference image; and determining a wheal measurement based on the contrast stretched difference image.

Figure 1A:
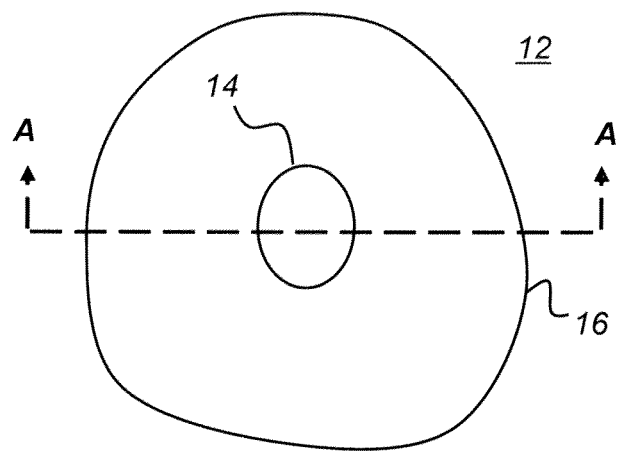
FIG. 1A is a top view showing wheal features in simplified schematic form.

It will be appreciated that for purposes of clarity and, where deemed appropriate, reference numerals have been repeated in the figures to indicate corresponding features. Illustrations are not necessarily drawn to scale. While methods and systems for skin test image analysis are described herein by way of example for several embodiments and illustrative drawings, those skilled in the art will recognize that the system and method are not limited to the embodiments or drawings described.

It should be understood, that the drawings and detailed description thereto are not intended to limit embodiments to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION

Embodiments of the present invention address the need for improved skin test image analysis such as that needed for allergy skin prick testing. The apparatus and methods of the present invention enable improved accuracy for detecting skin response and require only a small fraction of the area of the skin needed by conventional visual test methods and proposed using more compact test patch packaging.

The term "oblique", as used in the present disclosure, describes an angular relationship that is not parallel or normal, that is, other than an integer multiple of 90 degrees. In practice, two surfaces are considered to be oblique with respect to each other if they are offset from parallel or normal by at least about +/−10 degrees or more. Similarly, a line and a plane are considered to be oblique to each other if they are offset from parallel or normal by at least about +/−10 degrees or more.

In order to more fully understand aspects of the present invention, it is instructive to consider aspects of the measurement problem for allergen testing. Referring to the top view of FIG. 1A and the cross-sectional view of FIG. 1B, a positive reaction to an allergen at a skin prick site 12 is typically exhibited as a wheal 14 that is generally centered at site 12 and is bordered by an area of flare 16. Wheal 14 has fluidic content that lacks red blood cells so that it may appear somewhat different in color and can occupy an irregularly shaped area. Flare 16 has red blood cell content that is closer to the skin surface and can occupy an irregularly shaped area.

Figure 1B:
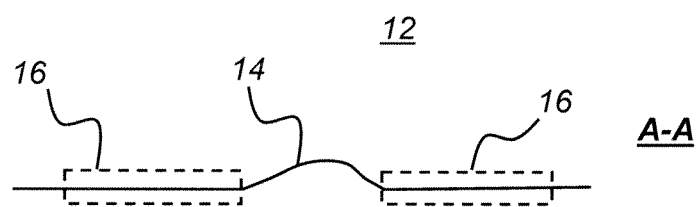
FIG. 1B is a cross-sectional side view of a wheal, showing wheal features in simplified schematic form.

Given the skin response structure described with reference to FIGS. 1A and 1B, the task of assessing skin prick site 12 with some accuracy requires some quantification of both contour and color area or dimensions. As has been noted previously, using conventional, visual methods of measurement, results can differ widely, even between experienced practitioners.

Figure 2A:
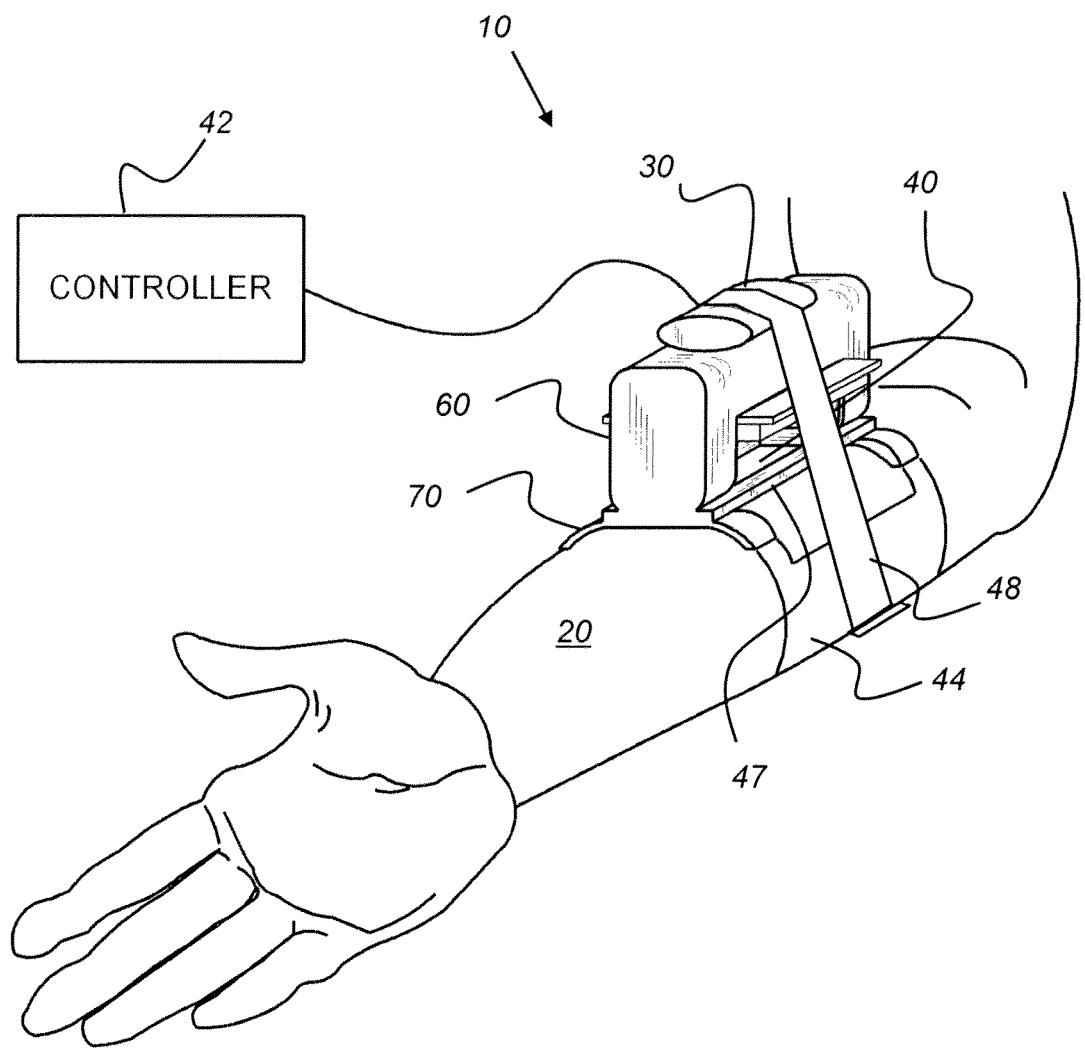
FIG. 2A is a perspective view of a skin testing apparatus on the arm of a patient according to one embodiment of the present invention.
Figure 2B:
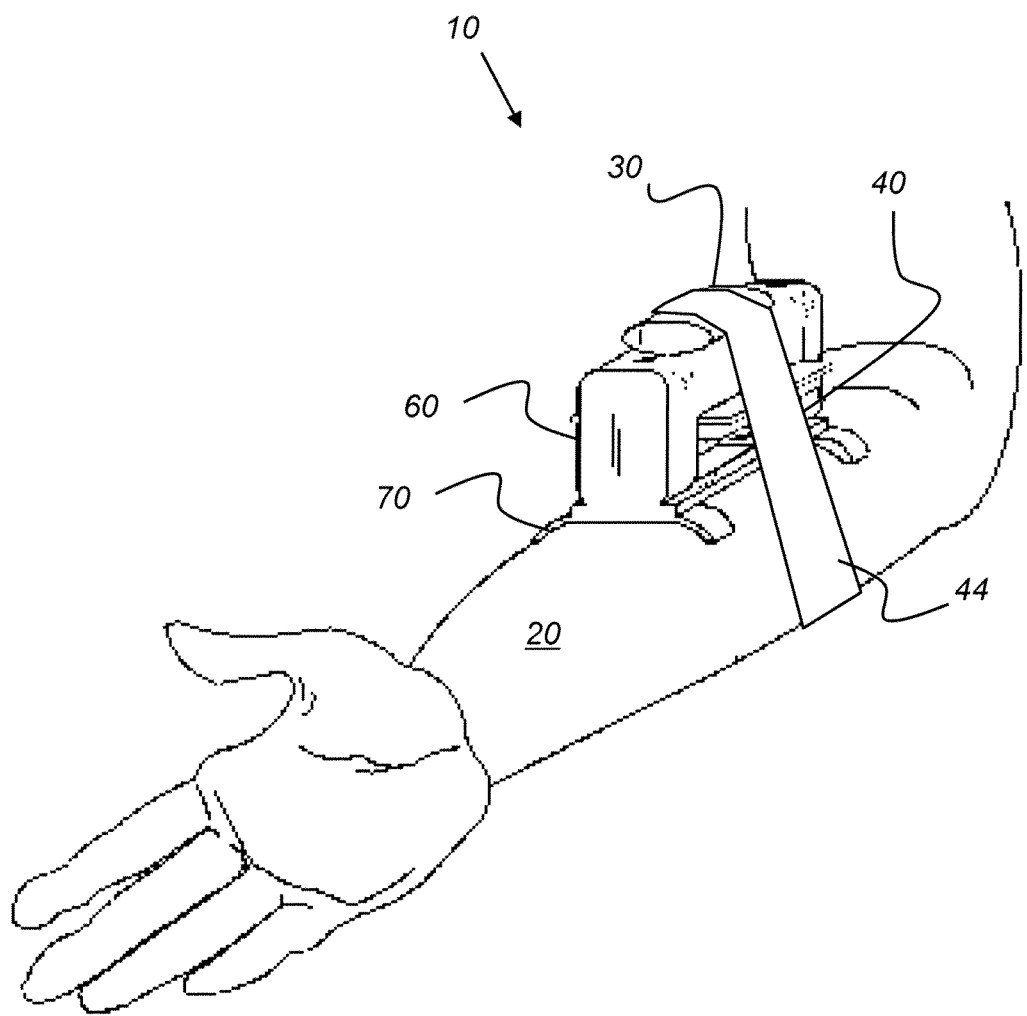
FIG. 2B is a perspective view of a skin testing apparatus on the arm of a patient according to an alternate embodiment of the present invention.
Figure 2C:
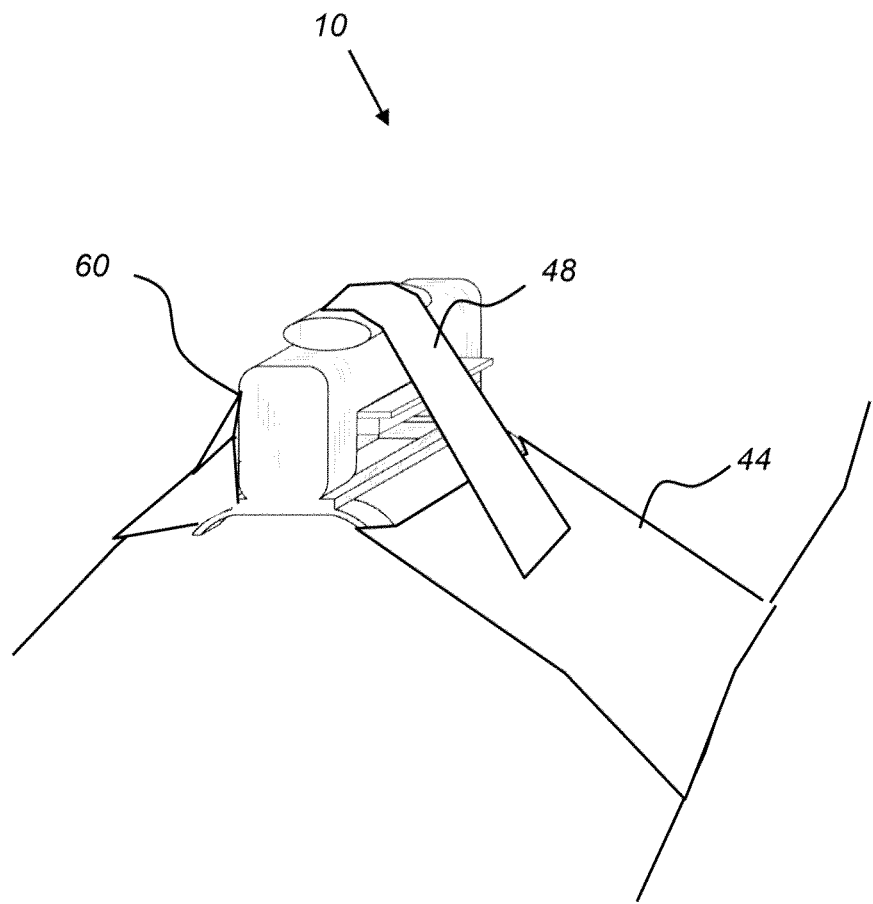
FIG. 2C is a perspective view of a skin testing apparatus on some other portion of the anatomy of a patient according to another alternate embodiment of the present invention.
Figure 3:
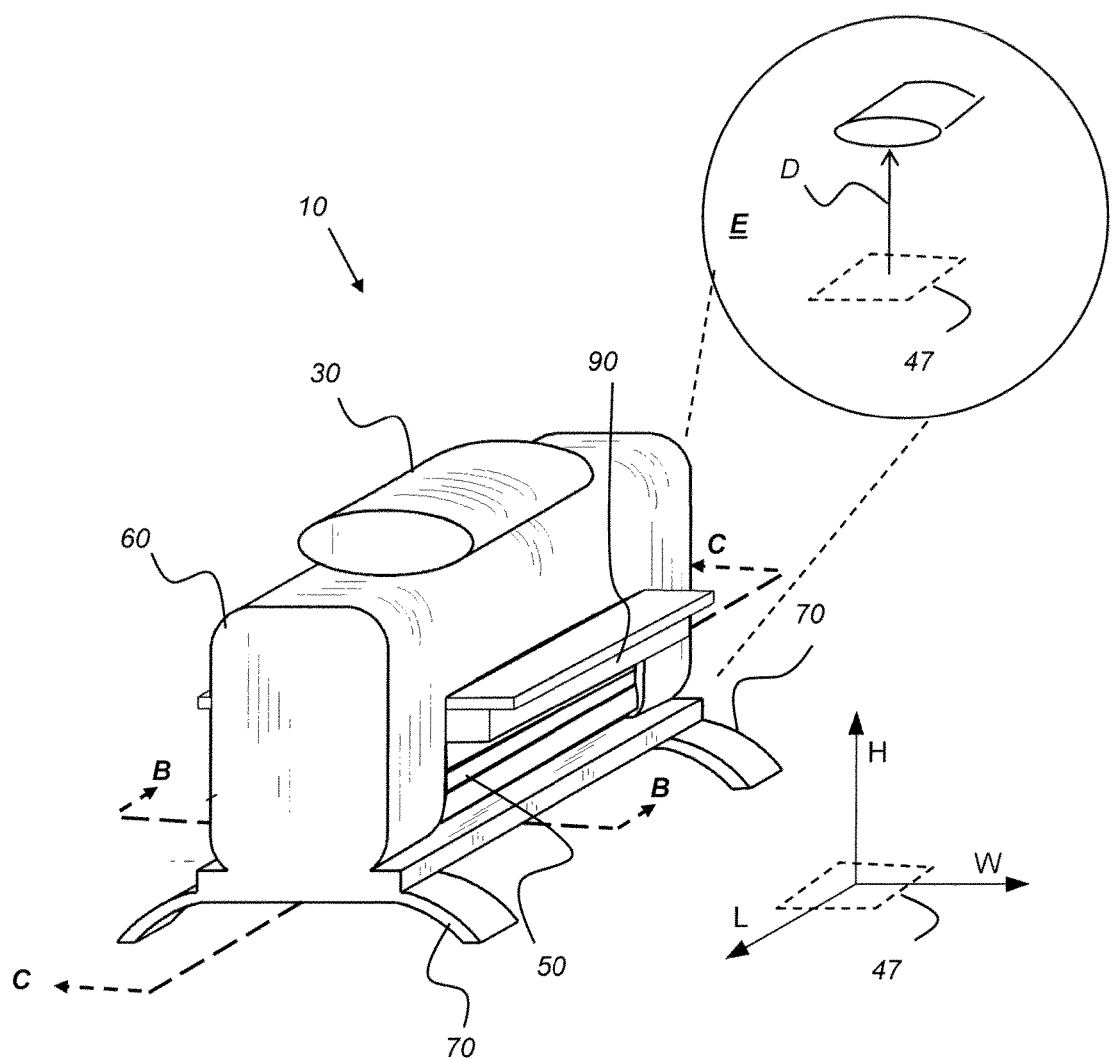
FIG. 3 is an enlarged perspective view of the skin testing apparatus shown in FIG. 2.

The perspective view of FIG. 2A shows a skin testing apparatus 10 in position against a skin surface position 47 of an arm 20 of a patient according to an embodiment of the present invention. FIG. 3 shows skin testing apparatus 10 in an enlarged view, with skin surface position 47 represented in dashed outline. A rigid housing 60 provides a light-tight cavity between an image sensing apparatus 30 and an opening 40. Opening 40 is releasably coupled against a skin surface position by a binding apparatus 44 using hook and loop fasteners, such as Velcro® straps, for example, or using some other suitable type of releasable coupling for securing housing 60 comfortably against the patient's skin. With the binding apparatus 44 movement of the opening 40 along the surface of the skin is precluded. The rigidity of the housing maintains a fixed distance between the image sensing apparatus 30 and the opening 40. An optional strap or band 48 also straps around image sensing apparatus 30 and the arm for fixing the optical distance between image sensing apparatus 30 and skin surface position 47 defined by opening 40. The band 48 applies pressure to the skin surface that constrains movement of the skin surface within the opening 40. Both the binding apparatus 44 and the band 48 act together to constrain both movement of the skin testing apparatus 10 relative to the skin surface position 47 and movement of the skin surface within the opening 40. Image sensing apparatus 30 cooperates with a control logic processor 42 that is in communication with image sensing components that generate image data for analysis, as described in more detail subsequently. In an optional embodiment, FIG. 2B shows another example of the binding apparatus 44 wrapped over image sensing apparatus 30. FIG. 2C shows housing 60 coupled to a skin surface position along the patient's back or other part of the body.

As is shown more clearly in FIG. 3, housing 60 also has a separate attachment member 70 that enhances the grip of housing 60 against arm 20 and may include means to protect the patients forearm from abrasion and a means to maintain comfort during the test. FIG. 3 also shows a representative coordinate system for mounting and locating skin testing apparatus. Width W and Length L axes lie along the surface of the skin at skin surface position 47. Height axis H defines the orthogonal axis to skin surface position 47.

Binding apparatus 44 shown in FIGS. 2A-2C maintains skin testing apparatus 10 in the plane defined by the Width and Length axes in FIG. 3, so that there is no relative movement along this plane, corresponding to the surface of the skin of the patient, during imaging. Another function of binding apparatus 44 is to maintain a substantially fixed optical distance between image sensing apparatus 30 and the skin surface at skin surface position 47 along height axis H. This function is needed because of the elastic nature of the skin surface and the fact that the skin surface adjusts its shape in response to the pressure or constraints applied to it.

Where skin testing apparatus 10 is bound to the patient's arm 20, as shown in FIGS. 2A and 2B for example, the distance between image sensing apparatus 30 and the surface of the skin defined by opening 40 at skin surface position 47 can vary by a few millimeters with normal arm movement and with load-bearing changes by the patient. For some types of imaging, this change in optical distance would be trivial and would have no impact on the image or its assessment. For applications such as allergy testing or assessment of subtle changes in skin features, however, a focus change or geometrical distortions of even less than a millimeter can be significant and, without some method for compensation, can make images difficult to process.

It is instructive to note that the relative elasticity of the skin, whether along the forearm or on other parts of the body, is a characteristic that distinguishes skin imaging from other types of imaging for which images captured in a time sequence must be registered to each other. As a coarse analogy, the skin surface can be compared with the surface of a bladder, readily changing shape in response to applied stress and constraints. This change of shape affects its relative curvature over a portion of its surface and can change the relative position of surface features, with time or due to slight human motion, complicating the task of maintaining proper focus and spatial registration of the image-sensing apparatus with the skin, such as that needed for accurate allergen response testing.

Figure 4A:
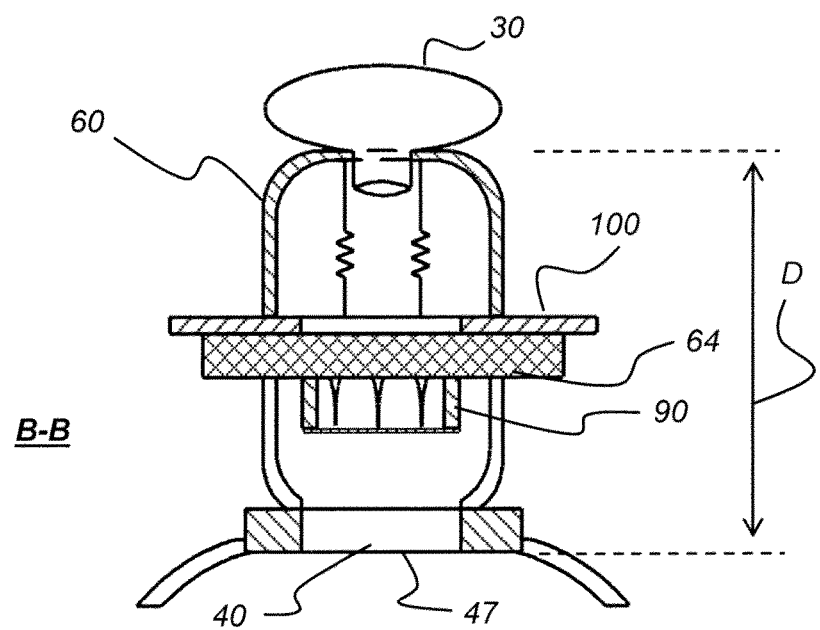
FIG. 4A is a transverse cross-sectional view of the skin testing apparatus that shows components internal to the housing, with particular focus on components used to introduce materials to the skin.

Consistent with an embodiment of the present invention, the optical distance D, shown in the inset E in FIG. 3 and in FIG. 4A, is fixed by securely banding image sensing apparatus 30 to the skin surface of the patient. Possible changes in skin surface curvature along the optical field, for example, are then made temporally invariant and are thus corrected for. This correction is achieved by corresponding movement of image sensing apparatus 30 components in consonance with skin surface changes. With respect to inset E in FIG. 3 and with respect to the cross-sectional view of FIG. 4A, distance D is thus maintained throughout the imaging session.

It should also be noted that binding apparatus 44 may have a different form where imaging is performed at skin surface position 47 along some alternate area of the skin, such as at a position along the patient's back, for example. As with imaging along the forearm shown in FIGS. 2A and 2B, binding apparatus 44 must provide a stable positioning of image sensing apparatus 30 at skin surface position 47 with respect to the three axes (Length L, Width W, and Height H) shown in FIG. 3.

In an alternate embodiment, the optical system of image sensing apparatus 30 has a built-in autofocus capability that adjusts for slight differences in focal distance and thus compensates for differences in patient position that might affect the height distance. In this embodiment, the positional shifts of skin features with respect to the imager along the skin surface are modeled, based on the measured auto-focus change, so that registration of captured images with the corresponding skin surface can be maintained.

A microlancet array or other type of skin test cartridge 90 is shown installed in housing 60; each microlancet is actuable to introduce a material, such as an allergen for example, to the exposed skin at the skin surface position, as described in more detail subsequently. A bellows or other type of movable baffle 50 is provided in order to help maintain a light-tight condition within housing 60, while allowing actuation of skin test cartridge 90.

Internal Housing Components for Introducing Materials to Skin

Figure 4B:
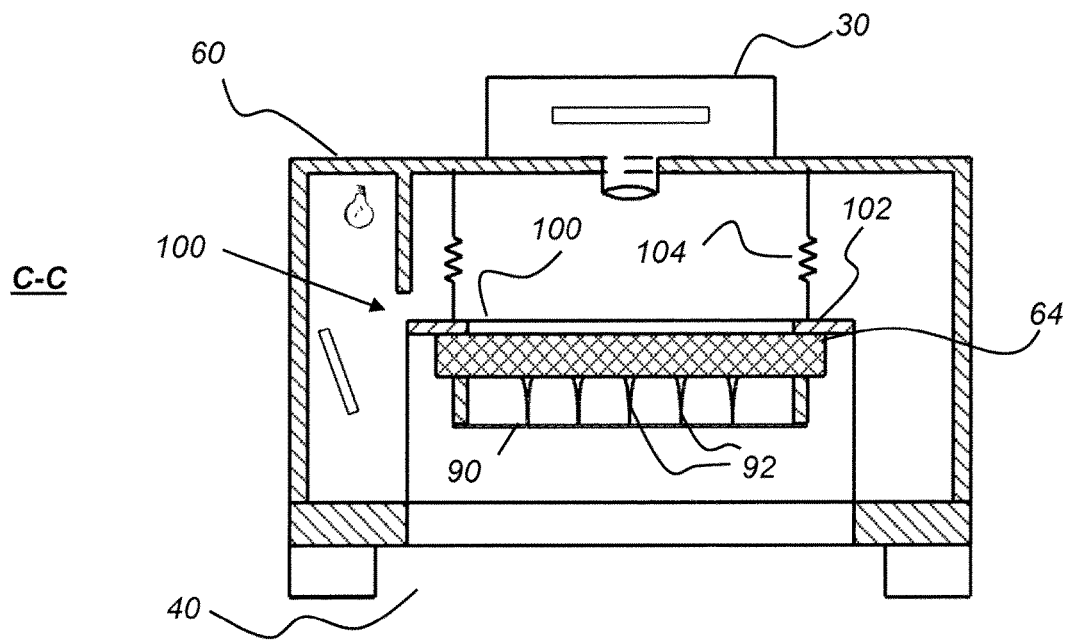
FIG. 4B is a longitudinal cross-sectional view of the skin testing apparatus that shows components internal to the housing, with particular focus on components used to introduce materials to the skin.

FIGS. 4A and 4B are mutually orthogonal cross-sectional views, transverse and longitudinal, respectively, that show components internal to housing 60, with particular focus on components used to introduce materials to the skin. Housing 60 provides mechanical support for microlancet array or other skin test cartridge 90 that can be installed and removed from a slot 64 in housing 60 as needed. The microlancet array has a number of microlancets 92 such as microneedles or other probing devices that are configured to introduce allergens or other test materials to the skin that is exposed at opening 40. Skin test cartridge 90 can be configured, for example, as described in commonly assigned U.S. Pat. No. 7,942,827 entitled "Minimally Invasive Allergy Testing System" by Mir et al. (Mir '827) which is herein incorporated by reference in its entirety. Skin test cartridge 90 may be, for example, a microneedle test cartridge, a contact test cartridge, an allergy test cartridge, and a microneedle cartridge with encapsulated or with coated allergens. Microneedles or microlancets may be closely spaced, within less than approximately 6 millimeters from each other, such as within 5 millimeters of each other. Other assembled arrays of fine needles may also be used, albeit with perhaps increased discomfort to the patient.

Introduction of a material to the skin may mean puncturing the surface of the skin or application of the test material onto well-defined areas of the skin surface, for example. Skin test cartridge 90, when configured as a microlancet array, includes microlancets 92, such as microneedles or other probing devices, with each microlancet 92 introducing a corresponding allergen or other test material. Mir gives a number of examples that show how microlancets and their corresponding allergen materials can be cooperatively packaged for test application.

Still referring to FIGS. 4A and 4B, an activator, such as a plunger mechanism 100 provides a mechanical stop 102 and spring force 104, both these bias elements biasing the activator away from the skin test area. Plunger mechanism 100 is moveably coupled to housing 60 and is configured to receive a skin test cartridge through the test cartridge opening, slot 64. The stop 102 and compressible components are shown schematically and can be configured in any of a number of ways, including those described in the US Patent Application Publication No. 2008/0269635 to Mir et al. which is herein incorporated by reference in its entirety.

Figure 5A:
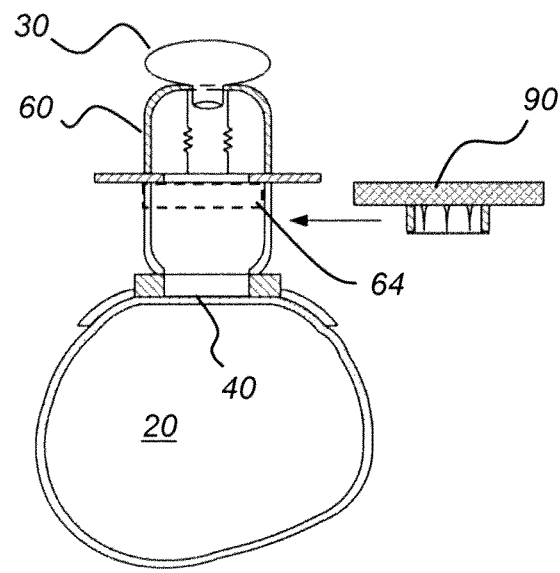
FIGS. 5A, 5B, 5C, 5D, and 5E show the sequence for using a microlancet array or other type of test cartridge to introduce the test material to the skin according to one embodiment of the present invention.
Figure 5B:
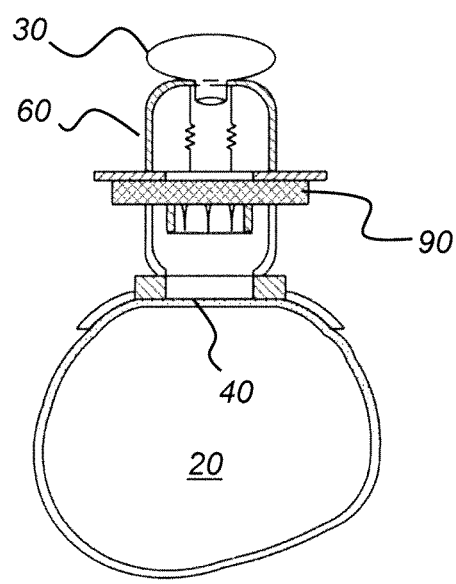
Figure 5C:
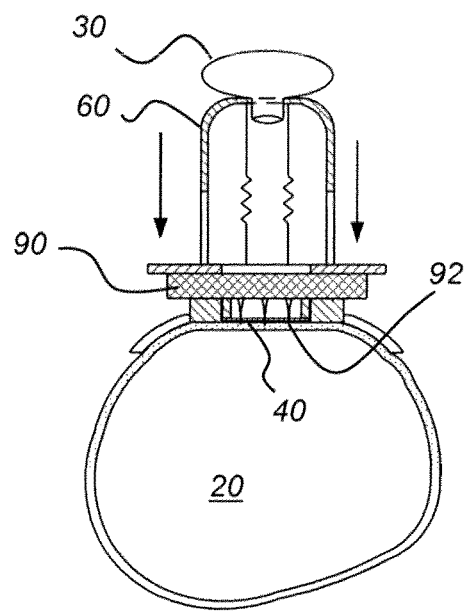
Figure 5D:
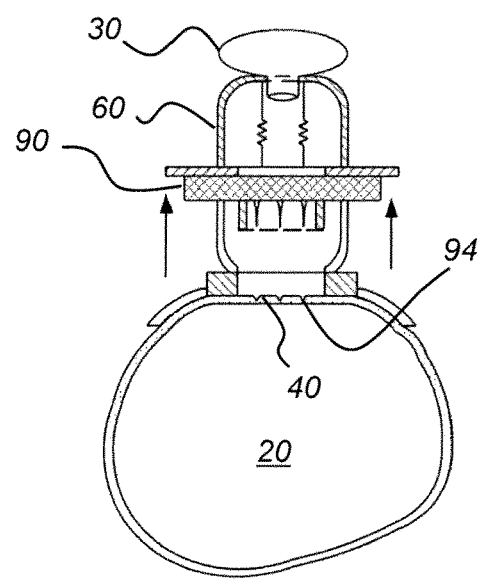
Figure 5E:
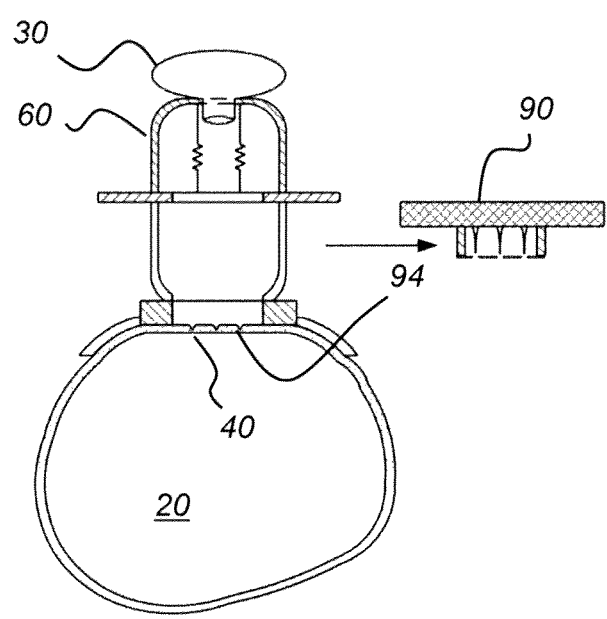

The sequence given in FIGS. 5A, 5B, 5C, 5D, and 5E shows how skin test cartridge 90 can be used to introduce the test material according to one embodiment of the present invention. The cross sectional view of FIG. 5A shows how skin test cartridge 90 can be installed into slot 64 within housing 60. FIG. 5B shows microlancet array as skin test cartridge 90 installed in position within housing 60, ready for actuation. FIG. 5C shows actuation, in which skin test cartridge 90 is moved toward opening 40 and introduces the allergen or other material to the skin. In the example shown, microlancets 92 puncture the skin surface. FIG. 5D shows skin test cartridge 90 retracted from the skin surface. A pattern of prick sites 94 is formed, as shown in FIG. 5D. FIG. 5E shows removal of skin test cartridge 90 from housing 60 at the end of this sequence.

With respect to the description and sequence shown in FIGS. 4A through 5E, it can be appreciated that there are a number of possible arrangements of skin test cartridge 90 and its microlancets 92 or other type of probing and application elements, including but not limited to those described in Mir '827 for example. At the end of the material introduction sequence, however performed, a pattern of test sites is produced on the exposed skin at opening 40. Imaging components of skin testing apparatus 10 are then used to assess skin response at each of the one or more test sites.

The Imaging Subsystem

FIGS. 6, 7A, 7B, and 7C show various aspects of an image forming apparatus 110 within housing 60 that is energizable to provide images for use by image processing image processing controller 42 (FIG. 2A) for assessing skin response. In this example, the image processing controller 42 includes a central processing unit (CPU) or processor, a memory, a user input device, a display, and an interface device which are coupled together by a bus or other link, although other numbers and types of systems, devices, components, and elements in other configurations and locations can be used. The processor in the image processing controller 42 executes a program of stored instructions for one or more aspects of the present technology as described and illustrated by way of the examples herein including by way of example only the method illustrated and described with reference to FIG. 10, although other types and numbers of processing devices and logic could be used and the processor could execute other numbers and types of programmed instructions.

The memory in the image processing controller 42 stores these programmed instructions for one or more aspects of the present technology as described and illustrated herein, although some or all of the programmed instructions could be stored and executed elsewhere. A variety of different types of memory storage devices, such as a random access memory (RAM) or a read only memory (ROM) in the system or a floppy disk, hard disk, CD ROM, DVD ROM, or other computer readable medium which is read from and written to by a magnetic, optical, or other reading and writing system that is coupled to the processor in the image processing controller 42, can be used for the memory in the image processing controller 42.

The user input device in the image processing controller 42 is used to input data and/or selections, although the user input device could be used to input other types of requests and data and interact with other elements. The user input device can include keypads, touch screens, and/or vocal input processing systems although other types and numbers of user input devices can be used. The display in the image processing controller 42 is a computer monitor, although other types and numbers of displays could be used. The interface device in the image processing controller 42 is used to operatively couple and communicate between the image processing controller 42 and the image sensing apparatus 30.

Although an example of a image processing controller 42 is described herein, it could be implemented on any suitable computer system or computing device. It is to be understood that the device of the example described herein is for exemplary purposes, as many variations of the specific hardware and software used to implement the examples are possible, as will be appreciated by those skilled in the relevant art(s).

Furthermore, the examples herein may be conveniently implemented using one or more general purpose computer systems, microprocessors, digital signal processors, and micro-controllers, programmed according to the teachings of the examples, as described and illustrated herein, and as will be appreciated by those ordinary skill in the art.

In addition, two or more computing systems or devices can be substituted for any embodiment of the examples herein. Accordingly, principles and advantages of distributed processing, such as redundancy and replication also can be implemented, as desired, to increase the robustness and performance of the devices and systems of the examples. The examples may also be implemented on computer device or devices that extend across any suitable network using any suitable interface mechanisms and communications technologies, including by way of example only telecommunications in any suitable form (e.g., voice and modem), wireless communications media, wireless communications networks, cellular communications networks, G3 communications networks, Public Switched Telephone Network (PSTNs), Packet Data Networks (PDNs), the Internet, intranets, and combinations thereof.

The examples may also be embodied as a non-transitory computer readable medium having instructions stored thereon for one or more aspects of the present technology as described and illustrated by way of the examples herein, as described herein, which when executed by a processor, cause the processor to carry out the steps necessary to implement the methods of the examples, as described and illustrated herein.

The image forming apparatus 110 comprises image sensing apparatus 30 and its supporting illumination and related components. Once skin test cartridge 90 is removed, housing 60 provides a light-tight cavity 62 between image sensing apparatus 30 and opening 40. The light-tight arrangement blocks ambient light from the imaging path, so that differences in ambient light conditions have a negligible effect on the images obtained by image sensing apparatus 30. Image sensing apparatus 30 includes an image sensor 112 and one or more optical elements 114, such as a lens, filter, polarizer, or other component for conditioning the image-bearing light from the object field defined at opening 40. Opening 40 lies against a skin surface position 72. Image sensor 112 is a CCD (Charge-Coupled Device) sensor in one embodiment. Other types of image sensors, such as CMOS (Complementary Metal-Oxide Semiconductor) devices are alternately used. The resolution of the imaging detector should be high enough to obtain images that can be assessed using the image processing algorithms, described in more detail subsequently. In one embodiment, for example, an image sensor of one or more megapixels is used.

Consistent with one embodiment of the present invention, image sensing apparatus 30 is a modular component that can be fitted into place in housing 60 and can be removed, such as during actuation of skin test cartridge 90, for example. Precise spatial registration of image sensing apparatus 30 with respect to the object field is provided in order to facilitate image processing and improve assessment accuracy, as is described in more detail subsequently.

Figure 7A:
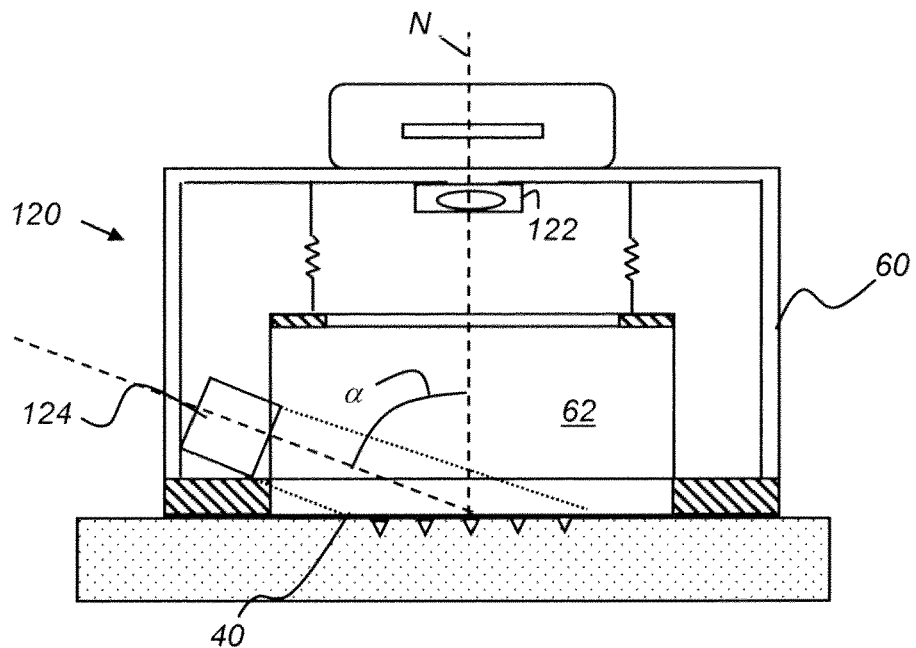
FIG. 7A is a longitudinal cross-sectional view that shows a portion of the illumination components used for imaging according to one embodiment of the present invention.

Image forming apparatus 110 also includes an illumination apparatus 120 that is energizable to direct suitable illumination toward exposed skin at opening 40 for obtaining images at image sensor 112. As shown in FIG. 7A, in illumination apparatus 120, a first light source 124 directs light that is substantially collimated and is directed toward opening 40 at an oblique angle α that is between about 45 degrees and 80 degrees from normal N. More preferably, oblique angle α is about 70+/−6 degrees from normal N. Substantially collimated light from light source 124 is at narrow angles, within about +/−15 degrees of the central angle that is at oblique angle α. With this configuration, light emitted from light source 124 is diffusely reflected from the skin surface, based on a Lambertian model for skin reflectance. Skin reflectance has both specular and diffuse components. The angle of incidence is variable at any point along the skin surface position at opening 40. With light at the oblique angles used; there is little or no effect from specular reflectance. First light source 124 has spectral content that is selected for improved sensitivity to contour. Laser, LED, incandescent, or fluorescent light sources that may include some collimating means may be used for first light source 124. Appropriately aligned polarizers may be placed at the source 124 and image sensor 112 to control specular reflection from the patient's skin that may hinder the measurements due to "glint spots".

Figure 7B:
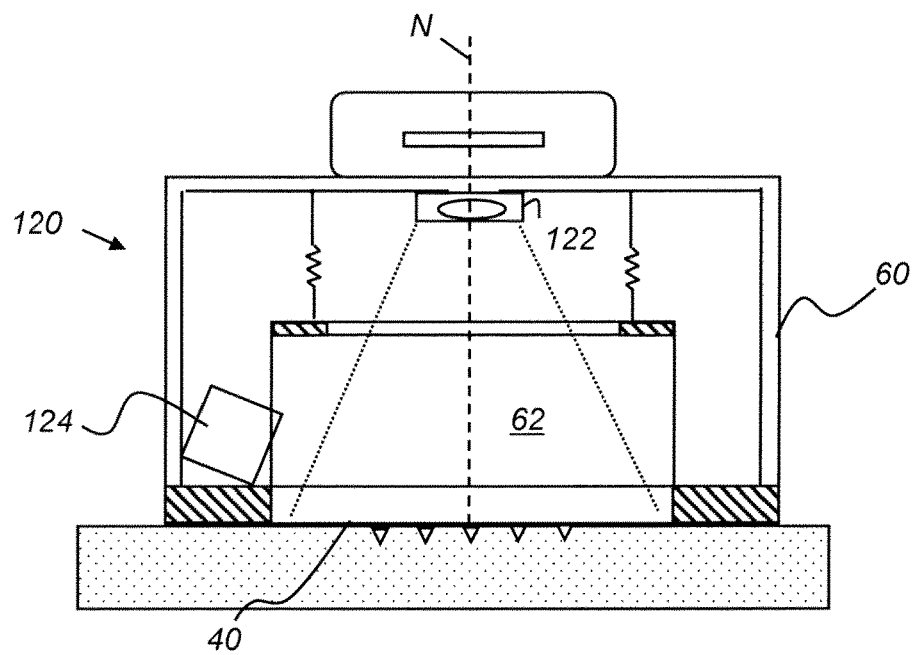
FIG. 7B is a longitudinal cross-sectional view that shows another portion of the illumination components used for imaging according to one embodiment of the present invention.

FIG. 7B shows an alternate arrangement with a second light source 122 that directs light toward opening 40 over an angular range that is substantially centered about a normal N to opening 40. The respective spectral bands of first and second light sources 122 and 124 may differ from each other according to one embodiment of the present invention. Second light source 122 has spectral content that is favorable for detection of flare, characterized by increased blood flow as described earlier with reference to FIGS. 1A and 1B. One or more Light Emitting Diode (LED) or other semiconductor light sources are used, with optional filters to condition the spectral content. Both diffuse and specular reflection from the skin surface can be used for obtaining an image using second light source 122.

Figure 7C:
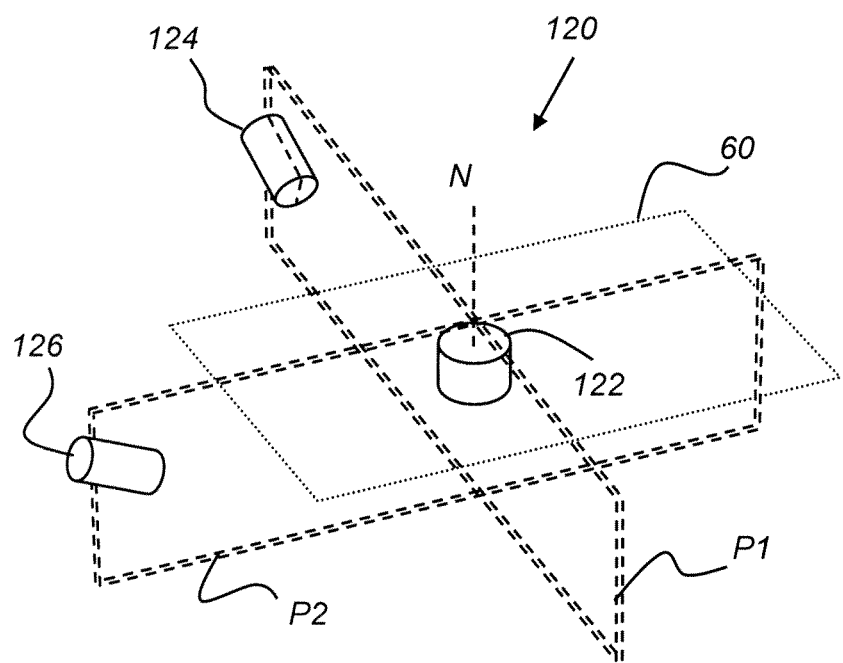
FIG. 7C is a partial perspective cutaway view that shows illumination components used for imaging according to an alternate embodiment of the present invention.

Referring to the perspective cutaway schematic of FIG. 7C, an arrangement of illumination apparatus 120 having a third light source 126 is shown. Light source 126 can have the same spectral characteristics as first light source 124 and direct light toward opening 40 at the same angle with respect to normal N as first light source 124. Light source 126 can be fixed in a rotated position about normal N from light source 124 and is preferably not in the same plane P1, but at some other angle, such as 90 degrees, along plane P2, as shown. In alternate embodiments, additional oblique light sources are provided to emit light toward opening 40 from three or more directions.

Light sources 122, 124, and 126 can be individual light-emitting elements, so that each is a laser or LED, for example. Alternately, one or more of light sources 122, 124, and 126 could be a combination of light sources, such as a combination of LEDs having different emitted wavelengths, for example. In one embodiment, light source 124 uses a combination having multiple LED sources, varying the amount of light provided from each individual LED source according to patient skin coloration, for example. Information initially sampled by image sensor 112 determines the skin color range that corresponds most closely to the patient, then actuates or energizes the appropriate combination of light sources based on the detected color range.

Object-to-Image Registration

Embodiments of the present invention are capable of providing measurement data for assessment of skin reaction to introduced allergens or other materials using a small fraction of the skin area required by conventional methods, including methods using a microneedle patch as described earlier with reference to Baldo '857 noted previously. Embodiments of the present invention use the combination of compact microlancet array packaging, fixed sensor position relative to the skin surface position, suitable illumination wavelengths and angles, and image processing techniques to allow allergen testing over a small portion of the patient's skin. By comparison with the device and teachings disclosed in the Baldo '857 patent cited earlier, in which an area of at least 9600 mm$^2$ is required for monitoring a 4×6 test patch array. In sharp contrast, illustrative examples of the present invention allow monitoring of a 4×6 test patch array within an area of only 600 mm$^2$ or less with spacing between test areas of about 15 mm or less is some examples, 10 mm or less in other examples, and 5 mm less in other examples. Benefits of requiring less area with the reduced spacing between sample sites include by way of example patient comfort and lower requirements for introducing potential allergens for testing well retaining improved accuracy, since with this technology the effects can still be accurately identified.

In order to provide this level of performance, a high degree of registration is maintained. Object-to-image registration is provided mechanically by binding apparatus 44, band 48, and attachment members 70 (described previously with reference to FIGS. 2A, 2B, and 3). These components cooperate to couple opening 40 against a fixed skin surface position and with a fixed optical distance between image sensing apparatus 30 and the skin surface position, so that subsequent jostling or movement of the patient during the skin test is unlikely to shift the respective position of opening 40 on the surface of the skin or to alter the curvature of the skin surface within opening 40 and so that focus and object-to-image registration are maintained for taking multiple images during testing. This physical constraint maintains the optical field that is imaged by image forming apparatus 110.

Figure 8A:
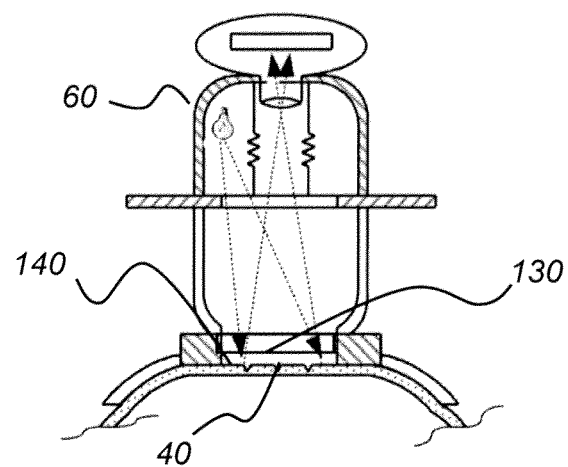
FIG. 8A is a transverse cross-sectional view of the housing of the skin testing apparatus showing the optional use of a skin attachment fixture.
Figure 8B:
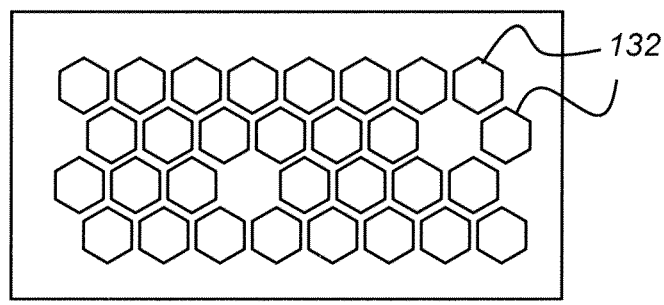
FIG. 8B is a plan view of a skin attachment fixture according to one embodiment of the present invention.

Referring to the cross-sectional view of FIG. 8A, an optional device for further aiding image quality as well as registration is a skin attachment fixture 130. Positioned across opening 40, skin attachment fixture 130 may be attached as part of housing 60 or, alternately, as a part of binding apparatus 44. FIG. 8B shows a plan view of skin attachment fixture 130 according to one embodiment of the present invention. In this arrangement, a number of apertures 132 are formed in fixture 130. Each aperture 132 frames a test site at which a microlancet or other probe introduces the allergen or other test material. With respect to the coordinate axes shown in FIG. 8A, this arrangement helps to register the position of the test site as fixed in the x-y plane. In addition to this, the use of skin attachment fixture 130 also flattens the optical field in the z axis (height H) direction, reducing field curvature in the object and thus providing a benefit for imaging optics of image forming apparatus 110.

As FIG. 8B shows, skin attachment fixture 130 may have an irregular array pattern of apertures 132, effectively blocking one or more microlancets 92 in skin test cartridge 90. This may be advantageous, for example, for skipping tests of certain allergens for a particular patient.

Figure 8C:
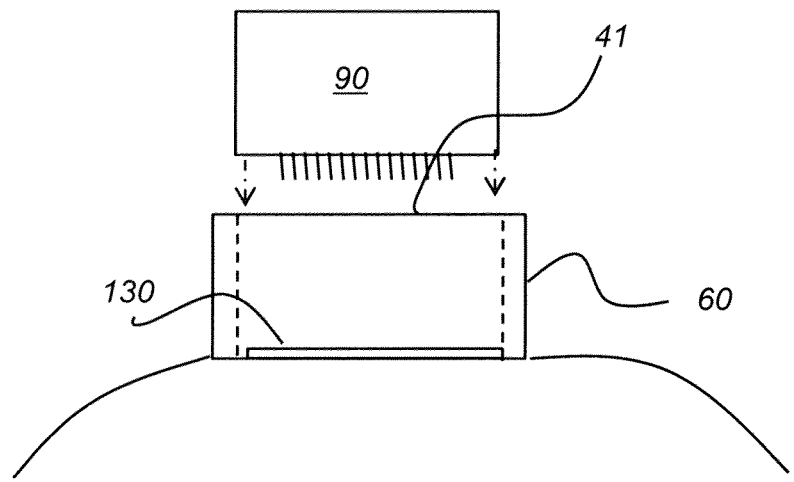
FIG. 8C is an exploded side view of a housing with a skin test cartridge.
Figure 8D:
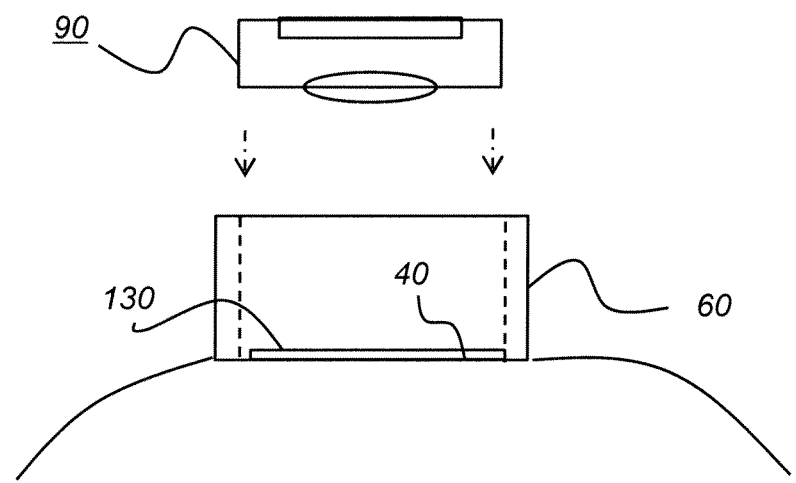
FIG. 8D is an exploded side view of a housing with an image sensing apparatus.

FIGS. 8C and 8D show housing 60 in an embodiment with skin attachment fixture 130 in place. Here, a top opening 41 in housing 60 accepts removable skin test cartridge 90 for applying the test material, then housing 60 accepts modular image sensing apparatus 30 for imaging. Skin attachment fixture 130 enables object-to-image registration to be maintained for these different functions in the testing procedure. Precise spatial registration of image sensing apparatus 30 with respect to the object field at opening 40 is provided in order to facilitate image processing and improve assessment accuracy, as is described in more detail subsequently.

Figure 8E:
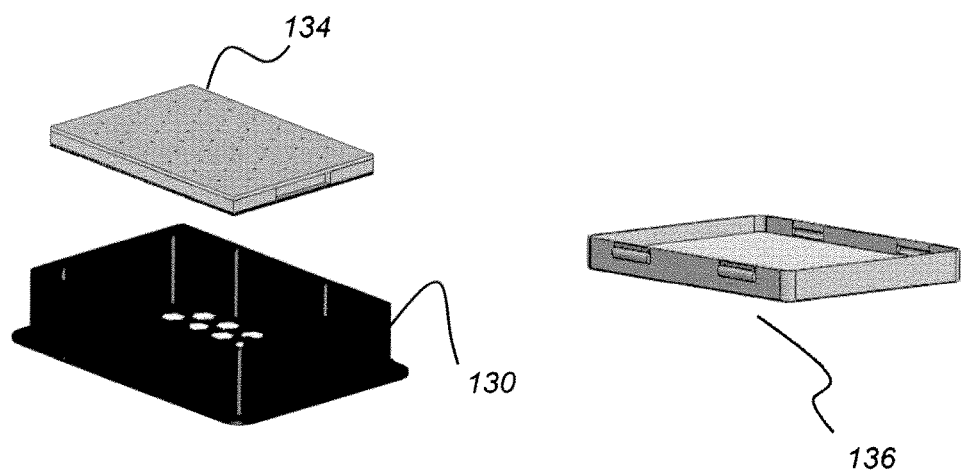
FIG. 8E is a perspective view of components that may optionally be disposable.

FIG. 8E shows skin test cartridge 90 in a disposable embodiment. Here, skin attachment fixture 130 is formed to hold a test cartridge 134 that can contain the microlancet array as well as the applied materials. An optional cover 136, preferably sterilized, is provided for image sensing apparatus 30. The components in FIG. 8E are disposable according to one embodiment of the present invention.

Referring again to the cross-sectional view of FIG. 8A, another optional aid for registration, usable in combination with skin attachment fixture 130 or separately, is a fiducial 140. FIGS. 9A, 9B, 9C, 9D, 9E, 9F, and 9G show examples of various types of fiducials 140 that can be provided. In one embodiment, a fiducial 140 is placed on the skin to create an absolute reference point. This is useful, for example, in the event that housing 60 is inadvertently shifted in position during the patient test. A fiducial 140 may include text or dimensional data for use as a positional reference. The use of fiducials in image registration is well known in the optical imaging arts.

Figure 9A:
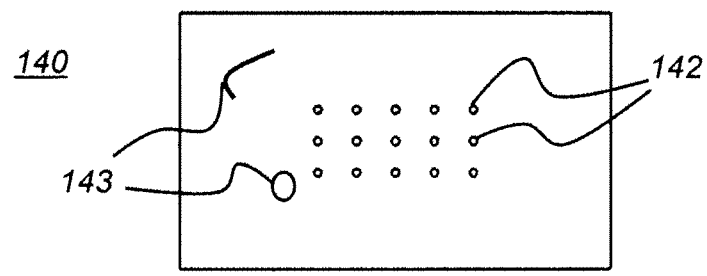
FIGS. 9A, 9B, 9C, 9D, 9E, 9F, and 9G show plan views of various types of fiducials used to aid registration according to various embodiments of the present invention.
Figure 9B:
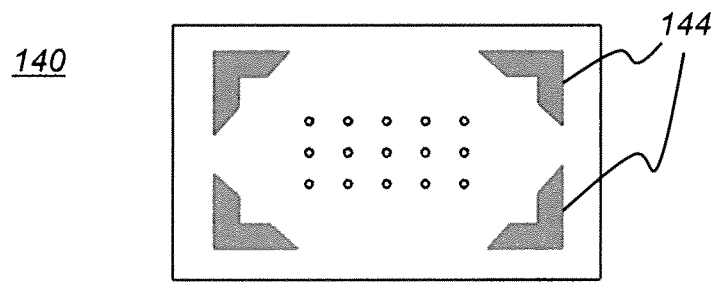
Figure 9C:
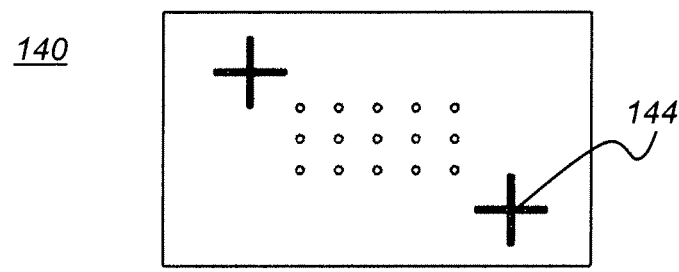
Figure 9D:
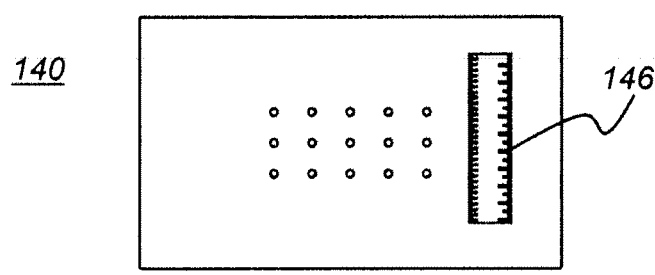
Figure 9E:
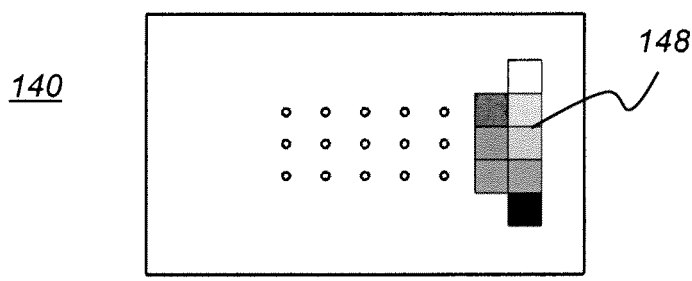
Figure 9F:
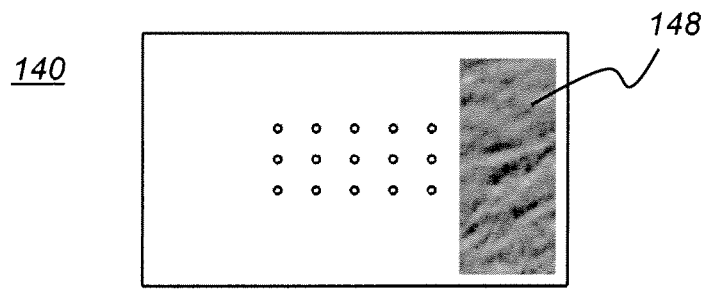
Figure 9G:
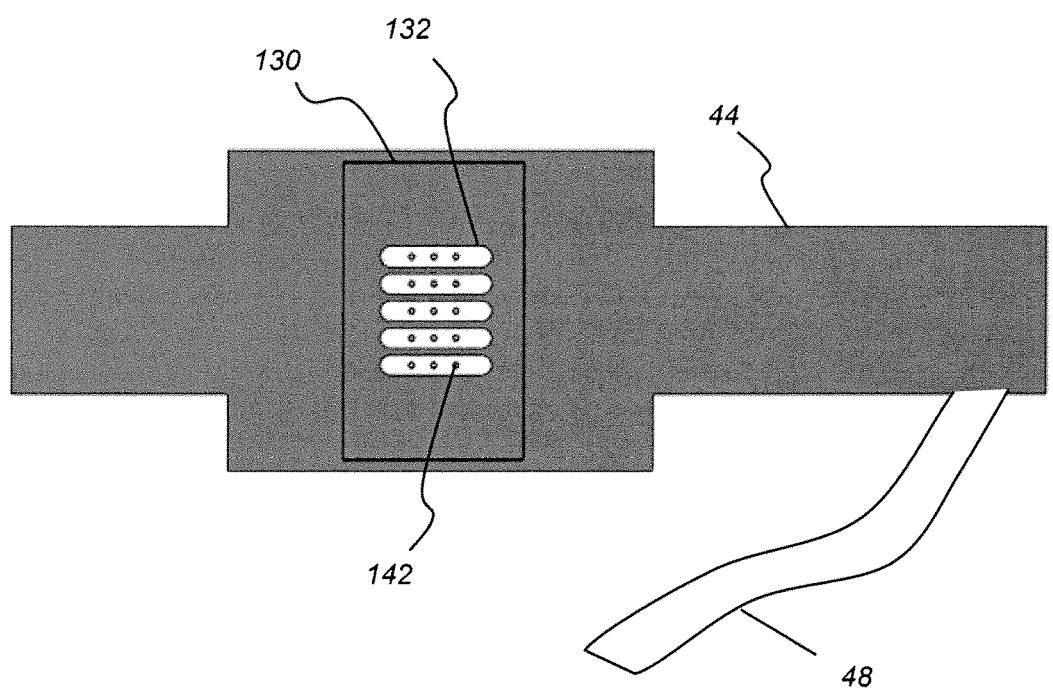

In practice, images captured by image forming apparatus 110 are then aligned, registered to the corresponding fiducial or fiducials 140. A particular fiducial 140 can be applied using a inked stamp that is applied to the skin as part of patient setup procedure or can be a sticker that is attached to the test area, such as when adjusting binding apparatus 44 (FIG. 2). Examples of various types of fiducials 140 used particularly for alignment positioning include the site markings 142 of FIG. 9A, reference coordinates 144 such as crosshairs or corner brackets shown in FIGS. 9B and 9C, and a ruling or measurement element 146 as shown in FIG. 9D. FIG. 9G shows the use of a combination of site markings 142 with skin attachment fixture 130. One or more openings 132 could alternately serve as a fiducial for alignment purposes. In an alternate embodiment, one or more skin features 143, such as pores, moles, or freckles, are used as fiducials, as shown schematically in FIG. 9A. Image processing algorithms can be used to enhance natural skin features to improve the contrast of the skin feature fiducial map. Further, because such skin features are found within the entire skin region being imaged, a map of linear and non-linear motion of the skin within the region can be generated for each data image captured. Known motion estimation algorithms can then be employed to cancel the linear and non-linear motion of the skin surface, if any, to maintain registration of the skin to the captured images, if the mechanical means to achieve registration disclosed above are insufficient in any particular case.

Images of the prick sites 94 may be used to establish the success or failure of the injection by a microlancet 92, thus providing a mechanism to determine whether the test is valid or not. Such images could be enhanced by the use of dyes or other materials placed in with the allergen, so as to enhance the visibility of the injection site. Additionally, the microlancets may be coated with such a material to enhance visibility of the skin prick site when injected. Alternatively, the microlancets may have regions surrounding the microneedle that cause the transfer of a dye or other contrast improving agent to the skin in areas that surround the prick site 94. By this mechanism a determination of the likelihood of a successful determination can be made by an examination of the surround pattern.

In addition to use as a positional aid, fiducial 140 may also or alternately provide benchmark measurements to aid image processing. This can be useful, for example, because the intensity and/or color balance of the light source can change over time or even over a single test for a multitude of reasons, such as power fluctuations and component aging, for example. By placing a gray scale or color reference target 148 within the image area, as shown in FIGS. 9E and 9F, the intensity variations can be compensated for accordingly. With target 148 as a color reference target, consistent color can also be obtained, as is well known to those skilled in color science. In addition, use of a color reference target, such as those used with the Munsell color system and the CIELAB system can help to compensate for other optical system differences.

Image Processing

Figure 10:
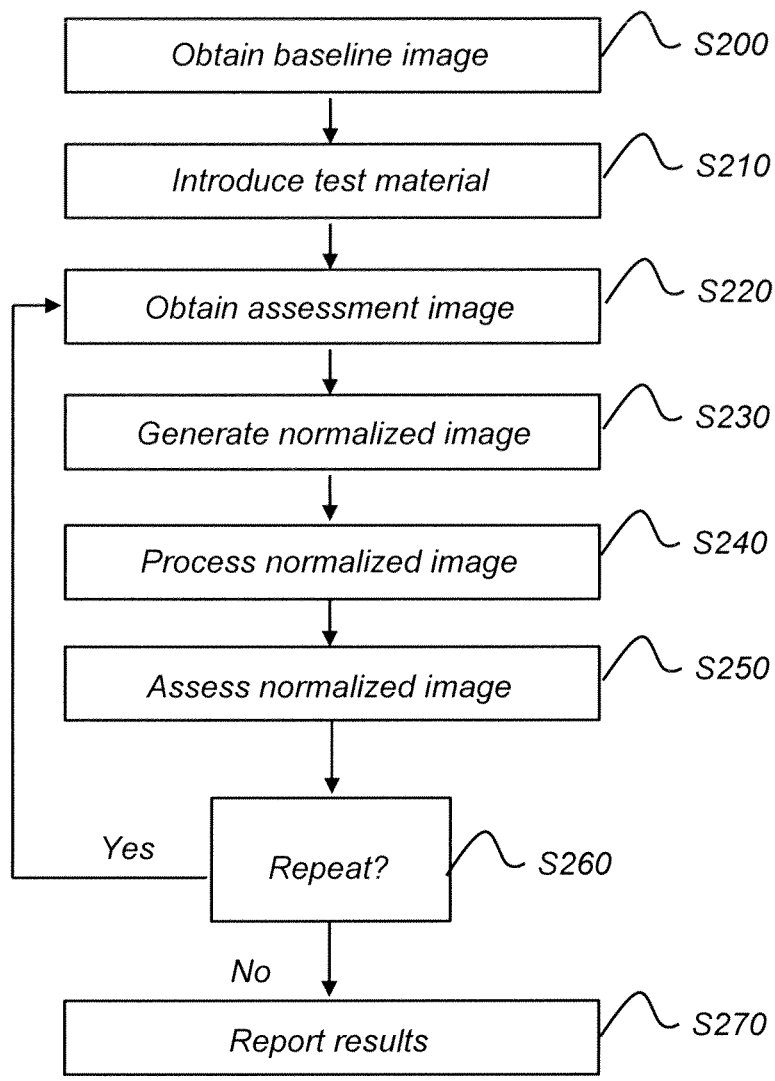
FIG. 10 is a logic flow diagram that lists a sequence used for obtaining and processing images in skin testing according to an embodiment of the present invention.

The logic flow diagram of FIG. 10 shows a sequence of steps used for image processing consistent with embodiments of the present invention. It is clear to those skilled in the image processing arts that the listed steps are exemplary and that changes to individual steps and to the image processing sequence itself can be affected within the scope of the present invention.

In order to provide skin testing of sufficient accuracy for allergen assessment and other functions, scaled object to image registration is needed for the two or more images of the skin that are obtained. For this reason, some mechanism or method for precise alignment of images obtained at different times is needed. Skin testing apparatus 10, described earlier with reference to FIGS. 2A-3, incorporate features that support object to image registration. Alternate methods for achieving this precision registration can include image processing algorithms that correlate two or more images, using techniques known in the art. However, such algorithms can err and result in inaccurate assessment data.

The description that follows applies when using skin testing apparatus 10 as the imaging device; a number of changes would be required when using a more general imaging apparatus for executing this sequence, as would be clear to those skilled in the image processing arts.

Figure 11A:
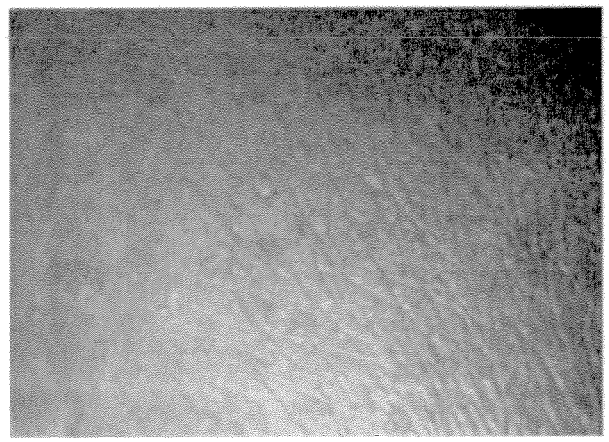
FIG. 11A is a plan view of a baseline image obtained in the image processing sequence.

An initial obtain baseline image step S200 captures a baseline image of skin surface position 47 at opening 40. Capturing this initial image enables subsequent processing to minimize or eliminate skin features that can confuse assessment steps, such as procedures needed for allergen testing, for example. By way of example, FIG. 11A shows a baseline image 150 for a patient about to undergo allergy testing. Using the skin testing apparatus 10 described herein above, the baseline image and subsequent images are obtained with first light source 124 (FIG. 7A). Alternately, one or more additional baseline images 150 and corresponding assessment images for processing can be obtained using second light source 122 or other light source.

Following this step, an optional introduce test material step S210 is executed, in which the test allergen, purified protein derivative, irritative substance, medical substance, unknown material, or other material is introduced against or within the skin surface. Using skin testing apparatus 10, for example, this step is executed in the sequence shown previously in FIGS. 5A through 5E. This step could be omitted, for example, for other types of skin monitoring, such as for observing or evaluating lesion growth. It should be noted that the term "baseline image" is a relative term that not only refers to the initial image that is obtained in a series of images, but more broadly can be applied to any image of the same skin surface position 47 that has been obtained at an earlier time than a particular "assessment image" and thus can serve as a reference for observing changes in the assessment image over a given time period.

Continuing with the FIG. 10 sequence, after an appropriate time period has elapsed, an obtain assessment image step S220 executes. A test image is captured for processing and assessment and is aligned with the baseline image for this purpose. Alignment of the two images is inherently performed when using skin testing apparatus 10 with binding apparatus 44 as described previously. Consistent with an alternate embodiment of the present invention, alignment is assisted using a fiducial 140, such as those described with reference to FIGS. 9A through 9G.

Figure 11B:
FIG. 11B is a plan view of an assessment image obtained after a time period.
Figure 11C:
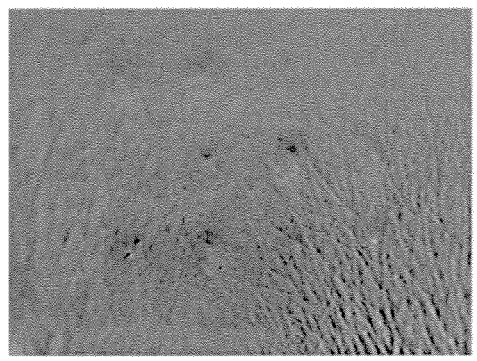
FIG. 11C is a plan view of a difference image obtained by processing the assessment image.

By way of example, FIG. 11B shows an assessment image 154, taken 15 minutes (t=15) after introduce test material step S210. As an initial processing step, a generate difference image step S230 combines the image data from the assessment image with the corresponding image data from the baseline image to generate a difference image. In one embodiment, this combination involves simple subtraction of the baseline image from the assessment image, so that the difference image that is generated against the baseline image shows the difference between the two images. FIG. 11C shows a difference image 160 that is obtained by subtracting the assessment image 154 of FIG. 11B from baseline image 150 of FIG. 11A. As part of normalization, noise reduction is also applied using filtering or other methods known to those skilled in the image processing arts.

Figure 6:
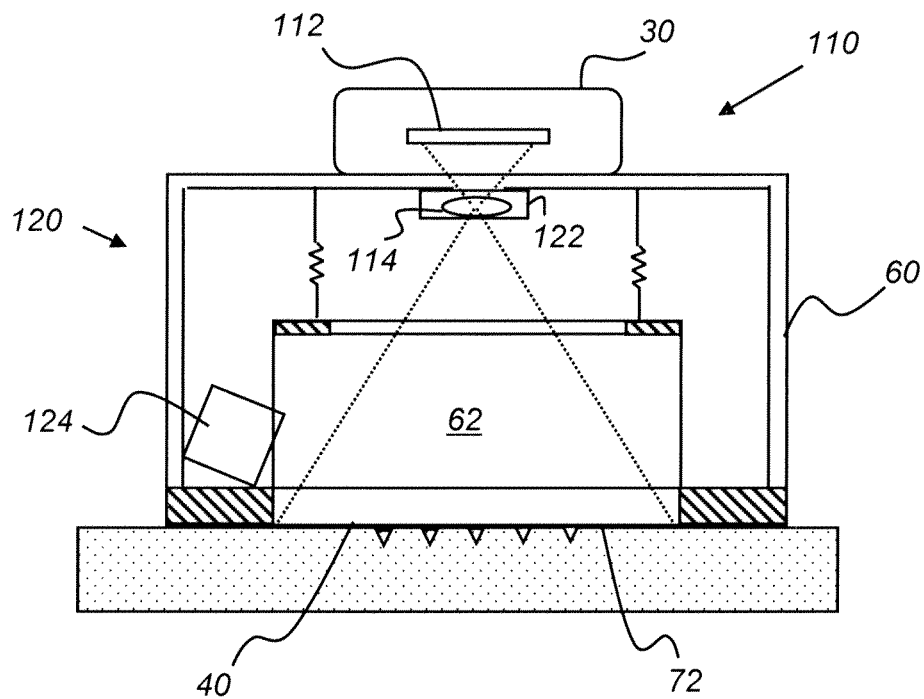
FIG. 6 is a cross-sectional view showing components of the image forming apparatus within the housing of the skin testing apparatus.

Once the difference image is obtained using the FIG. 10 sequence, a process difference image step S240 is executed. Processing of the difference image can take any of a number of different forms. Consistent with an embodiment of the present invention, normalizing includes processing to compensate for non-uniform spatial distribution of one or more illuminants in illumination apparatus 120 (FIGS. 6-7C). For example, this can comprise processing in forming the difference image itself, applying a Gaussian blur to either or both the baseline image and the assessment image before subtraction or other combination.

Figure 11D:
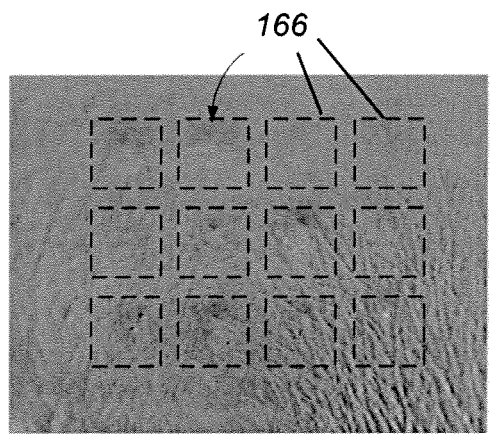
FIG. 11D is a plan view of segmentation of the difference image of FIG. 11C.

Consistent with an embodiment of the present invention, segmentation is used for defining one or more areas of interest in the difference image. Although not necessary, segmentation can be particularly useful for allergen testing, to identify each skin prick position so that the effect of each individual allergen can be accurately assessed. By way of example, FIG. 11D shows a segmented image 164, with each individual skin prick position 166 in a 3×4 matrix pattern shown in dashed outline.

Figure 12A:
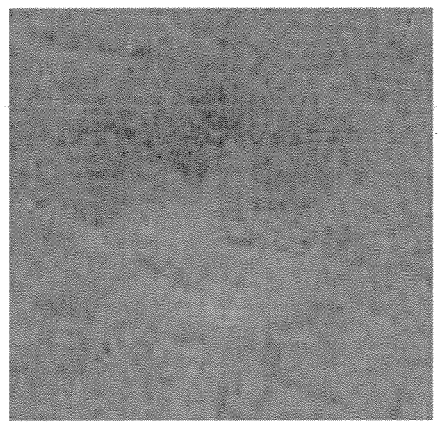
FIG. 12A shows an enlarged segment from the difference image.

Once segmented, each area of interest can be individually processed using a number of suitable image processing utilities. FIG. 12A shows one enlarged segment 170 from FIG. 11D, in which a wheal shows allergic reaction to a corresponding material. As can be seen from FIG. 12A, the wheal shape is somewhat indistinct, with a brighter region below and a darker region above and with some residual texture not eliminated in preceding steps. Additional processing is needed in order to allow some amount of measurement accuracy.

Figure 12B:
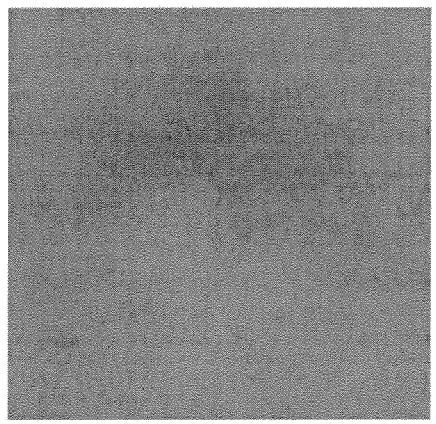
FIG. 12B show a filtered image from FIG. 12A.
Figure 12C:
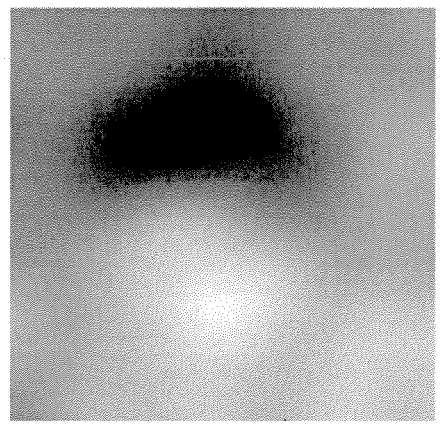
FIG. 12C shows an image of a wheal with contrast enhancement.

Consistent with one embodiment of the present invention, process difference image step S240 follows image segmentation with a Gaussian blurring process in order to filter out the residual texture shown in FIG. 12A. The results of a Gaussian blurring operation on this wheal image are shown as a filtered image 172 in FIG. 12B. FIG. 12C shows a subsequent processing procedure used to improve visibility of the wheal, applying a contrast stretch function to form a contrast stretched image 176. This processing helps to accentuate highlight brightness and low brightness values in the filtered image. Other contrast enhancement utilities could be used.

Figure 12D:
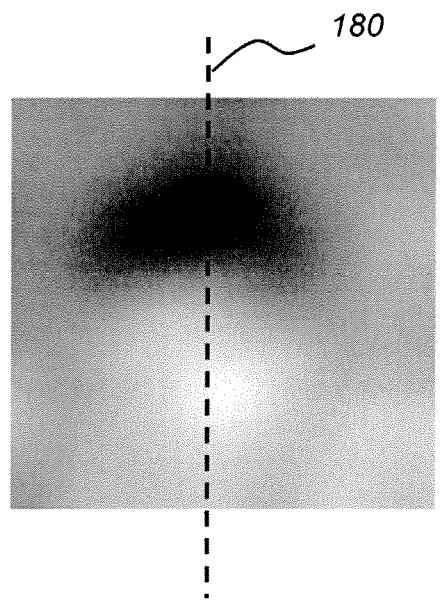
FIG. 12D shows obtaining a measurement along a line using the contrast enhanced image of a wheal.

Continuing further with the sequence of FIG. 10, an assessment step S250 can now be executed on contrast stretched image 176. The purpose of assessment step S250 is to obtain some measurement of the wheal or other skin feature of interest. FIG. 12D shows a vertical line 180 that is extended through the points of highest and lowest luminance, that is, through the extreme highlight and shadow areas of contrast stretched image 176.

Figure 13:
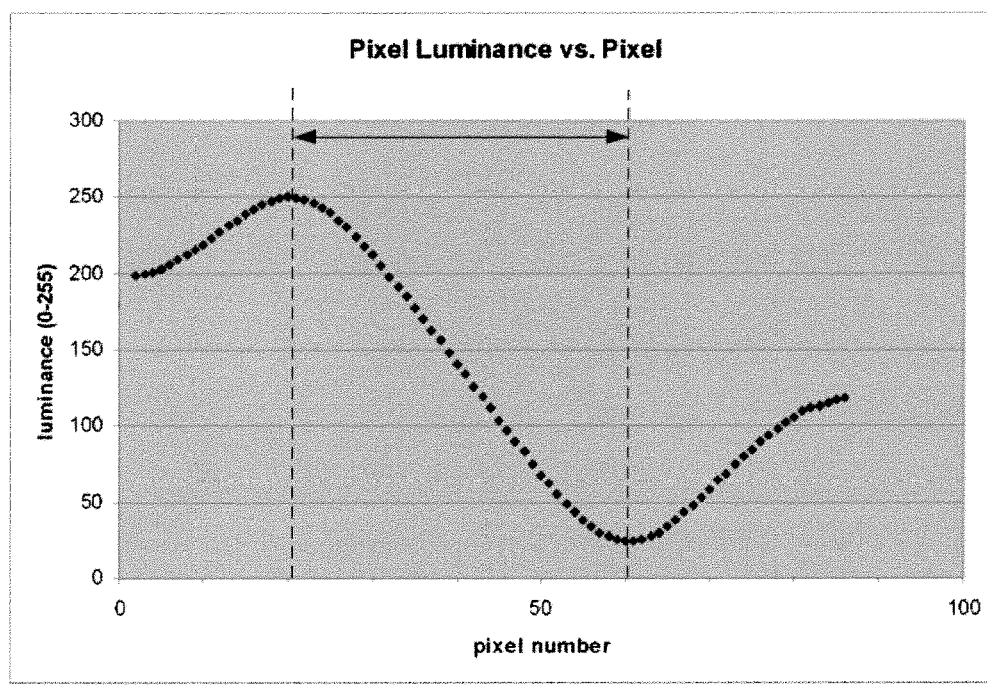
FIG. 13 shows a graph of pixel luminance taken along the line shown in FIG. 12D.

FIG. 13 shows a graph of pixel luminance obtained from this sampling. Pixels are assigned numbers in the vertical direction along this line, from the bottom to the top of the image in FIG. 12D. For this wheal, there is a distinct luminance maximum (highlight) at pixel #20, while there is a luminance minimum (shadow) at pixel #60. Since there are 40 pixels separating the high/low, and each pixel covers 45.4 microns at the image plane, the corresponding distance, a measure of wheal length in this direction, is approximately 1.82 mm. This provides one useful measure of wheal dimension in one direction.

It can also be useful to measure wheal dimensions in an orthogonal direction to that shown in FIG. 12D, so that both width and length dimensions can be obtained. For measurement in the orthogonal direction, a second series of images is obtained using illumination from an orthogonal direction, as was described earlier with reference to FIG. 7C. The same steps shown in the logic flow diagram of FIG. 10 would be duplicated for a second set of images, obtained using illumination at an orthogonal angle, as rotated about normal N.

Again referring to the general logic flow diagram of FIG. 10, a decision step S260 is shown, allowing for multiple assessment images to be obtained, processed, and assessed, using the sequence just described. In one embodiment of the present invention, assessment images are continually obtained and processed during an imaging session (using steps S220, S230, S240, and S250, for example), so that growth of a wheal or other skin feature can be observed, as described in more detail subsequently. At the conclusion of processing, a results reporting step S270 executes, in which results can be provided in some manner, reporting the skin feature measurement such as by display on an operator interface or recording in printed form or by storage in an electronic memory, for example. In addition to recording results, results reporting step S270 also records a history of steps executed in the skin testing sequence for a patient, in one embodiment. This enables subsequent testing for the patient to be executed using the same sequence, for example.

While the assessment method described with reference to FIGS. 12D and 13 provide an automated measure of wheal dimension which in practice provides measurements of much smaller skin reactions than the measurement typically recorded by a nurse or other practitioner. The manual or visual measurement that is typically obtained extends from one edge of the wheal to the other, rather than from points of lowest to highest luminance. For this reason, an alternate measurement strategy has proved to be useful.

Figure 14:
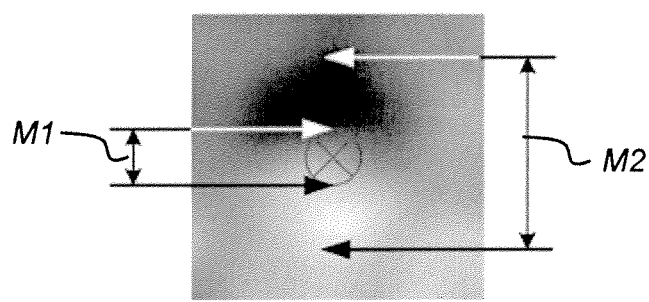
FIG. 14 is a plan view showing different measurements obtained from a wheal.

Referring to the plan view of FIG. 14, the difference between the automated luminance measurement M1 and visual measurement M2 is shown. To more accurately approximate the visual measurement M2, the derivative of the luminance measurement is used.

Figure 15:
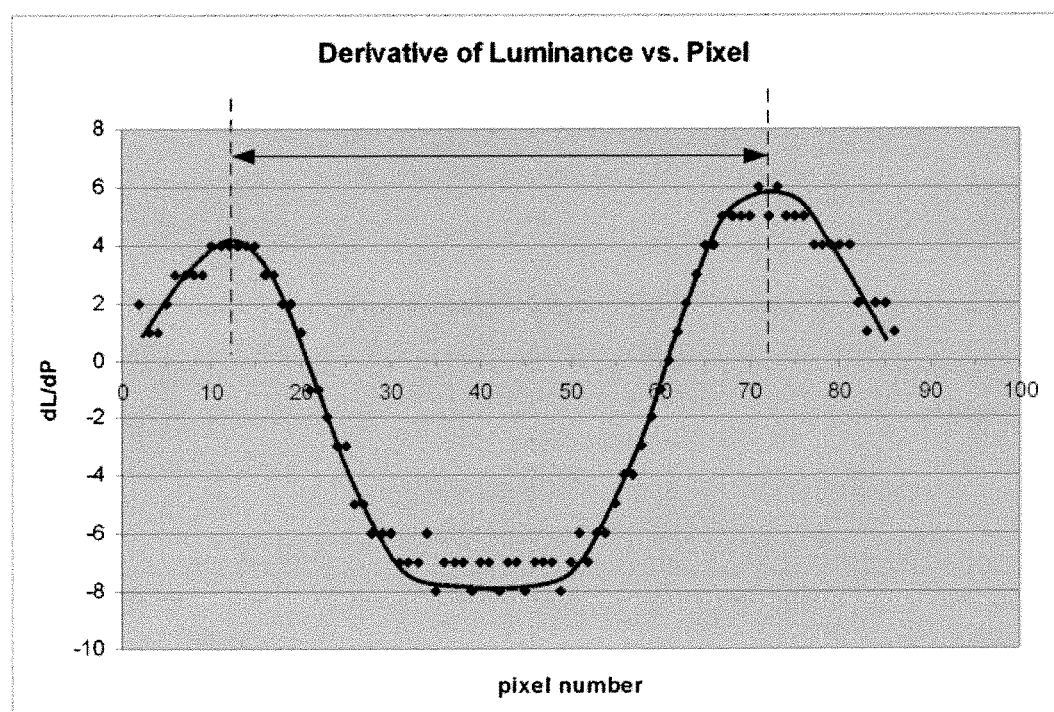
FIG. 15 is a graph that shows the derivative of luminance for the measurements of FIG. 13.

By way of example, the graph of FIG. 15 shows the derivative of the luminance (dL/dP) corresponding to the luminance measurements shown in FIG. 13. Of interest for measurement in FIG. 15 are the peak derivative values which indicate where the largest amount of change in pixel value occurs. For this wheal, the maximum luminance rate of change occurs at pixel #12, while another maximum luminance rate of change occurs at pixel #72 (produced at wheal edges). Since there are 60 pixels between the wheal edges and each pixel covers 45.4 microns at the image plane, vertical wheal diameter is approximately 2.72 mm. Dimensions obtained using this method have been shown to agree with careful manual measurements made directly on the actual wheal and using the captured "raw" image. For this particular wheal example, visual measurements are shown to be much closer to the 2.72 mm dimension shown using the derivative (FIG. 15) than to the 1.82 mm dimension obtained using highest and lowest luminance values (FIG. 13). Digital measurements obtained in this way have shown accuracies of ±2 pixels, or approximately ±90 microns. As is shown at pixel 72, some averaging of neighboring or nearby pixel values may be used to compensate for noise or other factors or to form a type of digital marking that can be correlated to the image itself.

Figure 16:
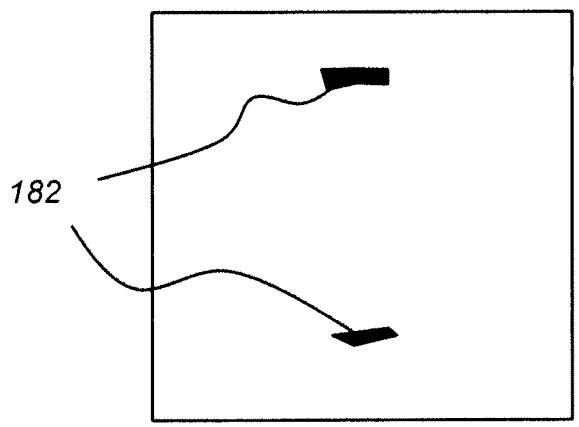
FIG. 16 shows digital fiducial marks, generated and applied to a view of the wheal image.
Figure 16:
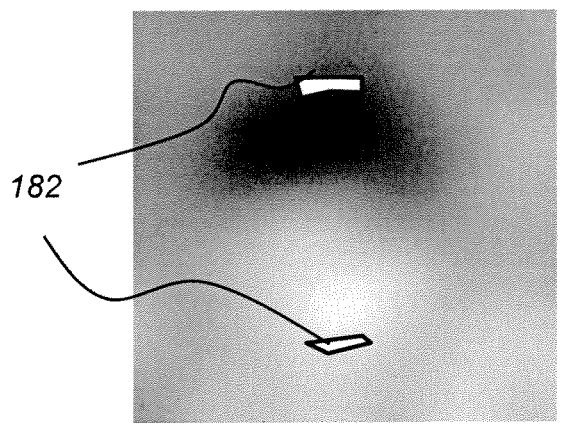

By way of example, FIG. 16 shows a set of digital fiducial marks 182 that are automatically generated using peak derivative values as shown in FIG. 15. Digital fiducial marks 182 can be displayed on the image itself or used by image processing software for obtaining dimensional measurements for a wheal or other skin feature.

Those skilled in the image processing arts can readily appreciate that the logic flow presented in FIG. 10 admits a number of possible variations and additional processing steps consistent with embodiments of the present invention. The sequence of images shown in FIGS. 17A and 17B show a set of processing steps used for allergen reaction skin testing in one embodiment.

Figure 17A:
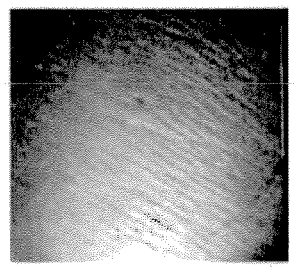
FIG. 17A shows a first set of processing steps used for allergen skin testing according to an embodiment of the present invention.
Figure 17A:
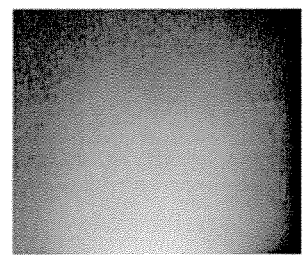
Figure 17A:
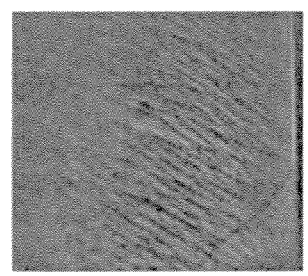
Figure 17A:
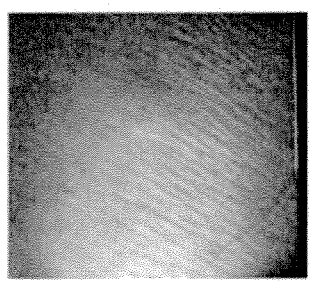
Figure 17A:
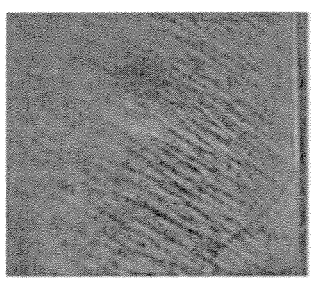

In the sequence beginning in FIG. 17A, baseline image 150 is obtained at the start of the test (time t=0), just following introduction of the allergen material using a microlancet array, as described previously. A blurred image 152 is obtained using a 27-pixel Gaussian blur filter on baseline image 150. A subtraction image 156 is then obtained by subtracting or otherwise combining blurred image 152 with baseline image 150. Assessment image 154 is captured after a suitable elapsed time period, here at time t=15 minutes. An interim difference image 158 is then generated by subtracting or otherwise combining assessment image 154 with blurred image 152. A bias value is also applied in this example.

Figure 17B:
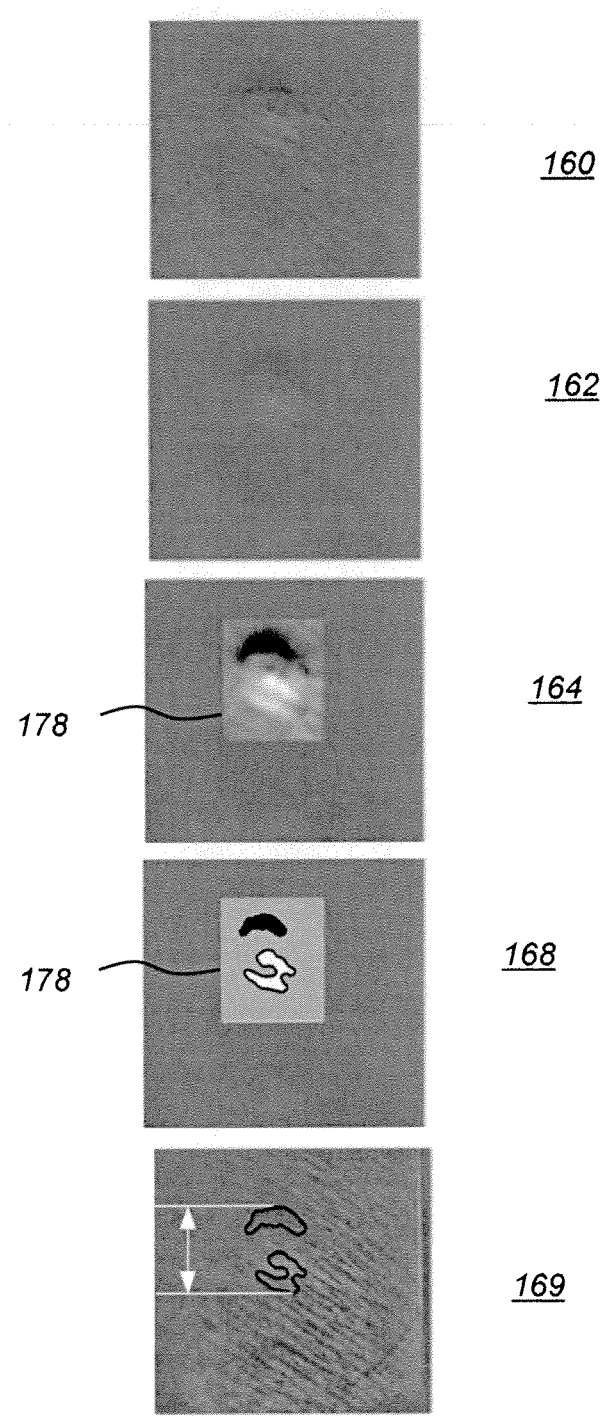
FIG. 17B shows a second set of processing steps used for allergen skin testing according to the embodiment of the present invention described with reference to FIG. 17A.

The processing sequence continues to FIG. 17B. Difference image 160 is obtained by subtracting or otherwise combining images 158 and 156 in the sequence shown in FIG. 17A. A conditioned image 162 is obtained by further filtering difference image 160 to help reduce high spatial-frequency noise. Segmented image 164 is generated automatically, based on known information about default skin prick location when using skin testing apparatus 10 (FIGS. 2A, 2B). A segmented region 178 is further processed to increase contrast, such as by contrast stretching as noted previously. An image 168 then shows segmented region with further conditioning to provide a binary mapped histogram that accentuates highlight (brightest) and shadow (darkest) areas of the image. An image 169 then shows further processing to outline the highlight and shadow areas for providing measurement of wheal dimensions. As was described earlier with reference to FIG. 15, the derivative can alternately be used to provide measurement points.

Flare Measurement

Embodiments of the present invention perform flare measurement using a spectral analysis of skin images. For flare measurement, illumination approximately normal to the surface has been found to be generally more accurate than illumination from an oblique angle, since it decreases reflectivity effects due to cos θ effects, as used for more accurate wheal contour measurement. Consistent with one embodiment of the present invention, light source 122 in FIG. 7B is used for flare measurement and has selectable spectral content, selected based on the detected skin coloration of the patient over the skin area that is being tested. For this purpose, light source 122 is a composite light source, having a set of LEDs that emit light of different respective wavelengths. A setting made by the operator or an initial measurement made by skin testing apparatus 10 itself is used to determine skin coloration over skin surface position 47. The appropriate LED or LEDs or other light sources are then selected. Various methods can be used to provide suitable amounts of light intensity from different LED or other light sources, including pulse-width modulation, for example.

Detection of flares, also known as erythemas, can be significantly enhanced if multispectral imaging methods are used that accentuate hyperemia coloration due to hemoglobin absorption. Hemoglobin's strong absorption peaks in the region of 540-590 nm can be used to advantage by using narrow sources that emit and/or are filtered in those wavelengths. Furthermore, color sensors such as CMOS and CCD devices have their own spectral characteristics that, unless taken into account, can lead to undesirable color channel signal mixing for the imaged flares. It has been found for example, that illumination sources such as filtered incandescent, fluorescent, or LED sources emitting in regions of interest such as 468 nm, 525 nm, 560 nm, 590 nm, 660 nm and narrow band filters at 540 nm, 565 nm, and 590 nm can yield significantly varying flare discrimination color signals when used with standard RGB-filtered Bayer image sensors. For Caucasian skin without much melanin, red and green sources in the spectral ranges >640 nm and ~540 nm yielded the greatest degree of flare contrast (highest signal-to-noise ratio SNR). For darker skinned patients having a greater amount of melanin content in their skin, green wavelength sources somewhat longer than 540 nm may be used to advantage since the combination of the monotonically decreasing absorption spectrum of melanin induces an effective shift in wavelength of the hemoglobin absorption line. Similarly, for wheal measurement, longer wavelength sources may be used for darker skinned patients to enhance the reflected signal (lower melanin absorption).

Figure 18A:
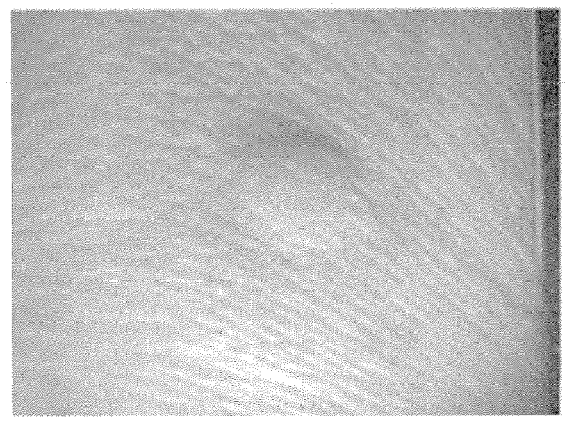
FIGS. 18A, 18B, and 18C show a sequence of steps used for flare detection and measurement according to an embodiment of the present invention.
Figure 18B:
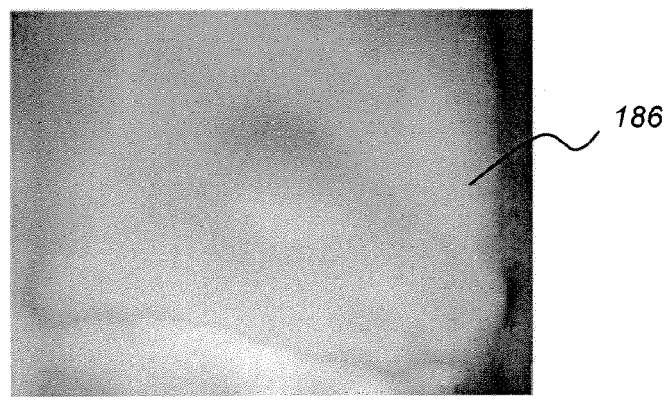
Figure 18C:
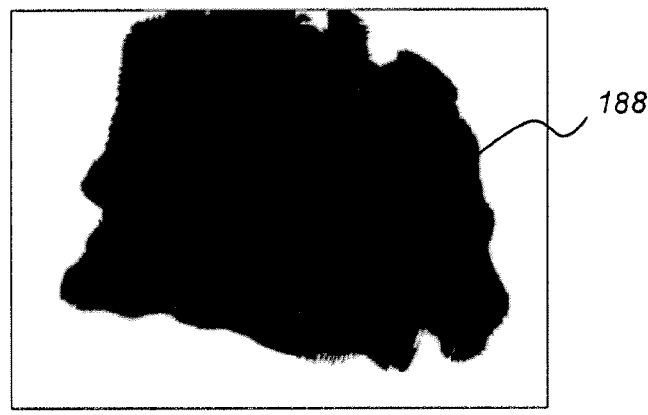
Figure 19:
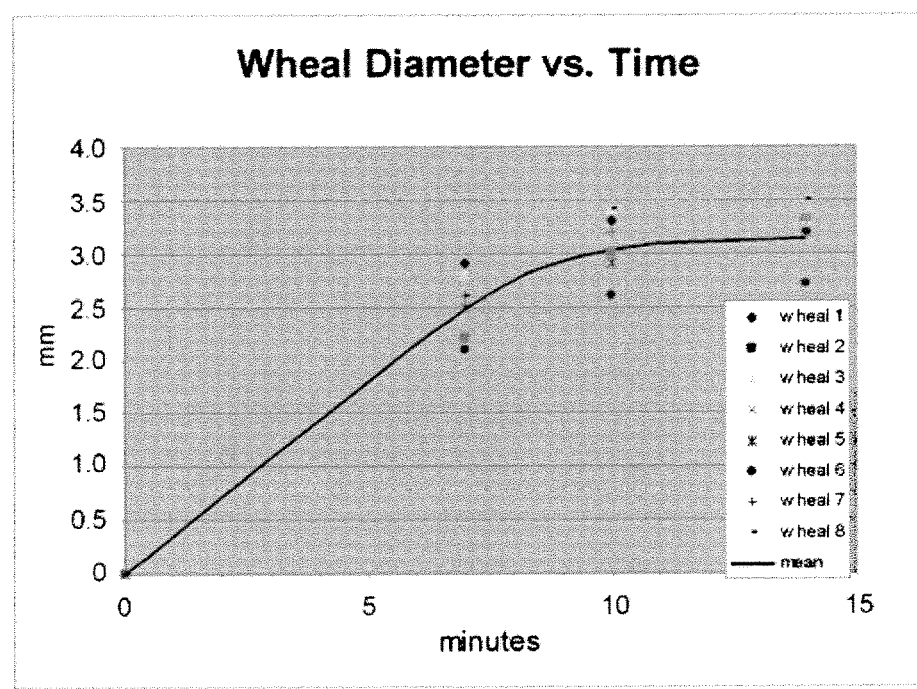
FIG. 19 is a graph showing wheal diameter over time.

FIGS. 18A, 18B, and 18C show a sequence of images related to flare measurement according to one embodiment of the present invention. An image 184 of the skin prick area is obtained as shown in FIG. 18A, using the selected light source 122. As FIG. 18B shows, the spectral content of the image is then used to detect a flare area 186. FIG. 18C shows a binary image 188 of the detected flare area. This image is obtained by applying a suitable threshold to the image data, such that pixels above this threshold are in one group (for example, black), pixels below this threshold are outside this group. To accurately determine the flare area, the number of pixels in the appropriate group can be counted and, using known data about pixel resolution, the total flare area computed. For the example shown in FIGS. 18A-18C, the following computations apply:

Total image area: 640×480 pixels=307,200 pixels
Each pixel area=$(0.05625 \text{ mm})^2$=0.003164 $\text{mm}^2$
Percentage of flare area to total image area=56%
Flare area=0.003164 $\text{mm}^2$×307,200×0.56=544 $\text{mm}^2$ One measurement that can be particularly useful for measuring allergen response relates to wheal growth over time. The graph of FIG. 19 shows an example that represents growth data of this type for different wheals in an allergy test sequence.

It is useful to review a number of observations relating to image processing using the apparatus of the present invention:

(i) For allergen response measurement and other applications, it is particularly advantageous to measure both the contour of a wheal or other skin feature and its color, as well as the color of the surrounding skin. This approach uses color image processing and can be distinguished from Doppler laser flowimetry methods that require a highly coherent light source for this purpose.

(ii) The contour of skin features is typically too subtle to allow direct measurement of shadow. Instead, a combination of diffuse and specular reflectance is used to determine contour changes.

(iii) Rates of change (derivative information) can be very useful for obtaining information on allergen response and for other types of skin testing. The apparatus and methods of the present invention allow both dimensional measurement at a point in time and, by obtaining and processing a succession of images, a measure of the rate of change in skin response.

Consistent with one embodiment of the present invention, an automatic image quality assessment is also performed as part of the image capture sequence. As one of these image quality checks, the relative flatness of the optical object field is assessed by image processing logic. To do this, the focus at a plurality of surface points along skin surface position is measured as one or more images are obtained. This provides a measure of relative image quality and is provided as part of results reporting step S270 (FIG. 10). A value indicative of the flatness of the object field can then be obtained by the user.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. An apparatus for skin testing comprising:
a housing with an opening configured to define a field of view of a skin testing region during use;
a test cartridge configured to be removably inserted into the housing, the test cartridge comprising a plurality of microneedles, wherein each of the plurality of microneedles is spaced one millimeter to fifteen millimeters apart from at least one other microneedle in the plurality of microneedles to generate a corresponding plurality of allergy test sample sites spaced one millimeter to fifteen millimeters apart in the field of view of the skin testing region, wherein the housing has an actuator apparatus integrated within the housing to manage actuation of the test cartridge within the opening of the housing when the test cartridge is removably inserted into the housing;
an image sensing apparatus positioned with respect to the housing to capture one or more images in the field of view provided by the opening in the housing;
an illumination apparatus positioned with respect to the housing to direct light towards at least a portion of the field of view provided by the opening in the housing;
a binding apparatus having one or more straps configured to detachably secure the housing to a body area having a circumference with the opening over the skin testing region and a band extending from the one or more straps and around the housing and the image sensing apparatus configured to apply pressure around the circumference of the body area and to a skin surface proximate the skin testing region to constrain movement of the opening over the skin testing region and to maintain a substantially fixed optical distance and spatial registration between the image sensing apparatus and the skin testing region; and
an image processing controller configured to execute one or more programmed instructions comprising:
obtaining, from the image sensing apparatus, a baseline image of the skin testing region prior to an assessment image of the skin testing region including the two or more allergy test sample sites of the corresponding plurality of allergy test sample sites generated by the plurality of microneedles of the test cartridge;
generating a difference image between the baseline image and the assessment image; and
analyzing the two or more allergy test sample sites of the corresponding plurality of allergy test sample sites generated by the plurality of microneedles of the test cartridge based on the difference image to provide a skin test result for each of the two or more allergy test sample sites based on the analysis.

2. The apparatus as set forth in claim 1 wherein the opening in the housing has an opening which is no more than 600 mm$^2$.

3. The apparatus as set forth in claim 1 wherein the housing further comprises a passage having a shape configured to removably receive the test cartridge.

4. The apparatus as set forth in claim 1 wherein the actuator apparatus further comprises:
a plunger engageable to move the test cartridge towards the skin testing region;
a stop positioned in the housing to limit the movement of the test cartridge towards the skin testing region; and
a biasing device configured to bias the plunger away from the skin testing region.

5. The apparatus as set forth in claim 1 wherein the housing further comprises a skin attachment fixture with an array of apertures which is detachably positioned across the opening in the housing.

6. The apparatus as set forth in claim 5 wherein the array of apertures of the skin attachment fixture has an irregular pattern.

7. The apparatus as set forth in claim 5 wherein the skin attachment fixture further comprises one or more fiducials.

8. The apparatus as set forth in claim 1 wherein the image sensing apparatus comprises one of a CCD image sensor or a CMOS image sensor.

9. The apparatus as set forth in claim 1 wherein the image processing controller is configured to analyze the two or more allergy test samples sites spaced one millimeter to ten millimeters apart in the field of view in each of the one or more captured images.

10. The apparatus as set forth in claim 9 wherein the image processing controller is configured to analyze the two or more allergy test samples sites spaced one millimeter to five millimeters apart in the field of view in each of the one or more captured images.

11. The apparatus as set forth in claim 1 wherein the illumination apparatus further comprises a first light source positioned at an oblique angle with respect to the opening to direct light toward the opening at the oblique angle from normal.

12. The apparatus as set forth in claim 11 wherein the illumination apparatus further comprises a second light source positioned to direct light toward the opening at substantially centered about normal.

13. The apparatus as set forth in claim 12 wherein the illumination apparatus further comprises a third light source positioned to direct light toward the opening at an oblique angle from normal and offset from the first light source.

14. The apparatus as set forth in claim 1 wherein the illumination apparatus is configured to provide substantially collimated light.

15. The apparatus as set forth in claim 1 wherein the binding apparatus further comprises an attachment member coupled to the housing configured to enhance a grip between the housing and the body area.

16. The apparatus as set forth in claim 1, wherein generating the difference image removes one or more image features less than one millimeter in size, resulting from focus changes or geometrical distortions, from the baseline image and the assessment image.

17. A method for making an apparatus for skin testing, the method comprising:
providing a housing with an opening configured to define a field of view of a skin testing region during use;
providing a test cartridge configured to be removably inserted into the housing, the test cartridge comprising a plurality of microneedles, wherein each of the plurality of microneedles is spaced one millimeter to fifteen millimeters apart from at least one other microneedle in the plurality of microneedles to generate a corresponding plurality of allergy test sample sites spaced one millimeter to fifteen millimeters apart in the field of view of the skin testing region, wherein the housing has an actuator apparatus integrated within the housing to manage actuation of the test cartridge within the opening of the housing when the test cartridge is removably inserted into the housing;

positioning an image sensing apparatus with respect to the housing to capture one or more images in the field of view provided by the opening in the housing;

positioning an illumination apparatus with respect to the housing to direct light towards at least a portion of the field of view provided by the opening in the housing;

providing a binding apparatus having one or more straps configured to detachably secure the housing to a body area having a circumference with the opening over the skin testing region and a band extending from the one or more straps and around the housing and the image sensing apparatus configured to apply pressure around the circumference of the body area and to a skin surface proximate the skin testing region to constrain movement of the opening over the skin testing region and to maintain a substantially fixed optical distance and spatial registration between the image sensing apparatus and the skin testing region; and providing an image processing controller configured to execute one or more programmed instructions comprising:

obtaining, from the image sensing apparatus, a baseline image of the skin testing region prior to an assessment image of the skin testing region including the two or more allergy test sample sites of the corresponding plurality of allergy test sample sites generated by the plurality of microneedles of the test cartridge;

generating a difference image between the baseline image and the assessment image; and analyzing the two or more allergy test sample sites of the corresponding plurality of allergy test sample sites generated by the plurality of microneedles of the test cartridge based on the difference image to provide a skin test result for each of the two or more allergy test sample sites based on the analysis.

18. The method as set forth in claim 17 wherein the providing the housing further comprises providing the housing with the opening which is no more than 600 mm$^2$.

19. The method as set forth in claim 17 wherein the providing the housing further comprises providing a passage having a shape configured to removably receive the test cartridge.

20. The method as set forth in claim 17 wherein the providing the actuator apparatus further comprises:

providing a plunger engageable to move the test cartridge towards the skin testing region;

positioning a stop in the housing to limit the movement of the test cartridge towards the skin testing region; and providing a biasing device configured to bias the plunger away from the skin testing region.

21. The method as set forth in claim 17 wherein the providing the housing further comprises providing a skin attachment fixture with an array of apertures which is detachably positioned across the opening in the housing.

22. The method as set forth in claim 21 wherein the providing the skin attachment fixture further comprises providing the skin attachment fixture with the array of apertures which have an irregular pattern.

23. The method as set forth in claim 21 wherein the providing the skin attachment fixture further comprises providing the skin attachment fixture with one or more fiducials.

24. The method as set forth in claim 17 wherein the positioning an image sensing apparatus further comprises providing the image sensing apparatus comprising one of a CCD image sensor or a CMOS image sensor.

25. The method as set forth in claim 17 wherein the providing the image processing controller further comprises providing the image processing controller configured to analyze the two or more allergy test samples sites spaced one millimeter to ten millimeters apart in the field of view in each of the one or more captured images.

26. The method as set forth in claim 25 wherein the providing the image processing controller further comprises providing the image processing controller configured to analyze the two or more allergy test samples sites spaced one millimeter to five millimeters apart in the field of view in each of the one or more captured images.

27. The method as set forth in claim 17 wherein the positioning the illumination apparatus further comprises positioning a first light source at an oblique angle with respect to the opening to direct light toward the opening at the oblique angle from normal.

28. The method as set forth in claim 27 wherein the positioning the illumination apparatus further comprises positioning a second light source to direct light toward the opening at an angle substantially centered about normal.

29. The method as set forth in claim 28 wherein the positioning the illumination apparatus further comprises positioning a third light source to direct light toward the opening at an oblique angle from normal and offset from the first light source.

30. The method as set forth in claim 17 wherein the positioning the illumination apparatus further comprises providing an illumination apparatus configured to provide substantially collimated light.

31. The method as set forth in claim 17 wherein the providing the binding apparatus further comprises providing an attachment member coupled to the housing configured to enhance a grip between the housing and the body area.

32. The method as set forth in claim 17, wherein generating the difference image removes one or more image features less than one millimeter in size, resulting from focus changes or geometrical distortions, from the baseline image and the assessment image.

* * * * *